(12) United States Patent
Gunderson et al.

(10) Patent No.: US 8,744,560 B2
(45) Date of Patent: Jun. 3, 2014

(54) ELECTROGRAM SUMMARY

(75) Inventors: Bruce D. Gunderson, Plymouth, MN (US); Karen J. Kleckner, New Brighton, MN (US); Kevin T. Ousdigian, Shoreview, MN (US); Amisha S. Patel, Maple Grove, MN (US); Julian Sanchez, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 70 days.

(21) Appl. No.: 13/250,676

(22) Filed: Sep. 30, 2011

(65) Prior Publication Data
US 2013/0085406 A1  Apr. 4, 2013

(51) Int. Cl.
*A61B 5/0456* (2006.01)

(52) U.S. Cl.
USPC .......................................................... 600/518

(58) Field of Classification Search
USPC ................................................. 600/518, 508
See application file for complete search history.

(56) References Cited

U.S. PATENT DOCUMENTS

| | | |
|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,734,382 A | 3/1988 | Krishna |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,193,550 A | 3/1993 | Duffin |
| 5,201,865 A | 4/1993 | Kuehn |
| 5,215,081 A | 6/1993 | Ostroff |
| 5,224,475 A | 7/1993 | Berg et al. |
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |

(Continued)

FOREIGN PATENT DOCUMENTS

WO   2006119340 A   11/2006

OTHER PUBLICATIONS

Office Action from co-pending U.S. Appl. No. 13/250,515 dated Mar. 13, 2013 (7 pages).
Catley et al., "Pronounced, Episodic Oxygen Desaturation, in the Postoperative Period: Its Association with Ventilatory Pattern and Analgesic Regimen," Anesthesiology 63:20-28, 1985.

(Continued)

*Primary Examiner* — Amanda Patton
(74) *Attorney, Agent, or Firm* — Michael C. Soldner

(57) ABSTRACT

The present disclosure is directed to generating and displaying an electrogram (EGM) summary for use by physicians or other clinicians. An implantable medical device (IMD) transmits EGM signal data for a number of cardiac episodes to an external computing device. The external computing device selects a subset of the cardiac episodes for which information or images are displayed to the user. In various examples, cardiac episodes may be selected for display based at least in part on a retrospective analysis classification of the cardiac episode.

32 Claims, 13 Drawing Sheets

(56) References Cited

U.S. PATENT DOCUMENTS

| | | |
|---|---|---|
| 5,324,315 A | 6/1994 | Grevious |
| 5,354,319 A | 10/1994 | Wyborny et al. |
| 5,379,776 A | 1/1995 | Murphy et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,509,927 A | 4/1996 | Epstein et al. |
| 5,527,344 A | 6/1996 | Arzbaecher et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,722,999 A | 3/1998 | Snell |
| 5,730,141 A | 3/1998 | Fain et al. |
| 5,741,311 A | 4/1998 | Mc Venes et al. |
| 5,755,735 A | 5/1998 | Richter et al. |
| 5,755,736 A | 5/1998 | Gillberg et al. |
| 5,755,739 A | 5/1998 | Sun et al. |
| 5,755,742 A | 5/1998 | Schuelke et al. |
| 5,776,168 A | 7/1998 | Gunderson |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,745 A | 10/2000 | Sun et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,250,309 B1 | 6/2001 | Krichen et al. |
| 6,266,554 B1 | 7/2001 | Hsu et al. |
| 6,270,457 B1 | 8/2001 | Bardy |
| 6,301,503 B1 | 10/2001 | Hsu |
| 6,317,632 B1 | 11/2001 | Krig et al. |
| 6,317,633 B1 | 11/2001 | Jorgenson et al. |
| 6,358,203 B2 | 3/2002 | Bardy |
| 6,393,316 B1 | 5/2002 | Gillberg et al. |
| 6,434,428 B1 | 8/2002 | Sloman et al. |
| 6,445,952 B1 | 9/2002 | Manrodt et al. |
| 6,449,508 B1 | 9/2002 | Sheldon et al. |
| 6,470,210 B1 | 10/2002 | Chen et al. |
| 6,477,417 B1 | 11/2002 | Levine |
| 6,480,745 B2 | 11/2002 | Nelson et al. |
| 6,493,586 B1 | 12/2002 | Stahmann et al. |
| 6,599,250 B2 | 7/2003 | Webb et al. |
| 6,607,485 B2 | 8/2003 | Bardy |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,669,631 B2 | 12/2003 | Norris et al. |
| 6,699,187 B2 | 3/2004 | Webb et al. |
| 6,721,600 B2 | 4/2004 | Jorgenson et al. |
| 6,748,269 B2 | 6/2004 | Thompson et al. |
| 6,760,624 B2 | 7/2004 | Anderson et al. |
| 6,788,971 B1 | 9/2004 | Sloman et al. |
| 6,842,645 B2 | 1/2005 | Dalal |
| 6,865,141 B2 | 3/2005 | Tada et al. |
| 6,974,413 B2 | 12/2005 | Bardy |
| 6,980,860 B2 | 12/2005 | Stadler et al. |
| 7,047,083 B2 | 5/2006 | Gunderson et al. |
| 7,069,085 B2 | 6/2006 | Cao et al. |
| 7,167,747 B2 | 1/2007 | Gunderson et al. |
| 7,187,790 B2 | 3/2007 | Sabol et al. |
| 7,206,633 B2 | 4/2007 | Saba |
| 7,212,849 B2 | 5/2007 | Zhang et al. |
| 7,236,828 B2 | 6/2007 | Casavant et al. |
| 7,242,978 B2 * | 7/2007 | Cao et al. .................. 600/518 |
| 7,266,409 B2 | 9/2007 | Gunderson |
| 7,286,997 B2 | 10/2007 | Spector et al. |
| 7,289,851 B2 | 10/2007 | Gunderson et al. |
| 7,333,855 B2 | 2/2008 | Gunderson et al. |
| 7,353,063 B2 | 4/2008 | Simms, Jr. |
| 7,369,893 B2 | 5/2008 | Gunderson |
| 7,430,446 B2 | 9/2008 | Li |
| 7,480,529 B2 | 1/2009 | Li |
| 7,539,540 B2 | 5/2009 | Gunderson et al. |
| 7,567,835 B2 | 7/2009 | Gunderson et al. |
| 7,582,061 B2 | 9/2009 | Li et al. |
| 7,738,950 B2 | 6/2010 | Johnson et al. |
| 7,894,883 B2 | 2/2011 | Gunderson et al. |
| 2001/0007053 A1 | 7/2001 | Bardy |
| 2001/0031997 A1 | 10/2001 | Lee |
| 2001/0037366 A1 | 11/2001 | Webb et al. |
| 2002/0077561 A1 | 6/2002 | Jamar et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0050563 A1 | 3/2003 | Suribhotla et al. |
| 2003/0074026 A1 | 4/2003 | Thompson et al. |
| 2003/0204215 A1 | 10/2003 | Gunderson et al. |
| 2004/0006278 A1 | 1/2004 | Webb et al. |
| 2004/0015197 A1 | 1/2004 | Gunderson |
| 2004/0064161 A1 | 4/2004 | Gunderson et al. |
| 2004/0088018 A1 | 5/2004 | Sawchuk et al. |
| 2004/0088374 A1 | 5/2004 | Webb et al. |
| 2004/0093240 A1 | 5/2004 | Shah |
| 2004/0106955 A1 | 6/2004 | Swerdlow et al. |
| 2004/0120557 A1 | 6/2004 | Sabol et al. |
| 2004/0122297 A1 | 6/2004 | Stahmann et al. |
| 2004/0122484 A1 | 6/2004 | Hatlestad et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0022181 A1 | 1/2005 | Fox et al. |
| 2005/0033385 A1 | 2/2005 | Peterson |
| 2005/0049910 A1 | 3/2005 | Lancaster et al. |
| 2005/0060193 A1 | 3/2005 | Lancaster et al. |
| 2005/0075902 A1 | 4/2005 | Wager et al. |
| 2005/0080347 A1 | 4/2005 | Sheth et al. |
| 2005/0137485 A1 | 6/2005 | Cao |
| 2005/0137636 A1 | 6/2005 | Gunderson et al. |
| 2005/0154421 A1 | 7/2005 | Ousdigian |
| 2005/0159785 A1 | 7/2005 | Rueter |
| 2005/0192506 A1 | 9/2005 | Kim et al. |
| 2005/0192836 A1 | 9/2005 | Rossinni et al. |
| 2005/0192844 A1 | 9/2005 | Esler et al. |
| 2005/0228693 A1 | 10/2005 | Webb et al. |
| 2006/0064020 A1 | 3/2006 | Burnes et al. |
| 2006/0074331 A1 | 4/2006 | Kim et al. |
| 2006/0074454 A1 | 4/2006 | Freeberg |
| 2006/0074464 A1 | 4/2006 | Subera et al. |
| 2006/0074465 A1 | 4/2006 | Webb |
| 2006/0116732 A1 | 6/2006 | Gunderson et al. |
| 2006/0116733 A1 | 6/2006 | Gunderson et al. |
| 2006/0217621 A1 | 9/2006 | Kim et al. |
| 2006/0217769 A1 | 9/2006 | Saba |
| 2006/0235476 A1 | 10/2006 | Gunderson et al. |
| 2006/0281998 A1 | 12/2006 | Li |
| 2007/0061393 A1 | 3/2007 | Moore |
| 2007/0112276 A1 | 5/2007 | Simms |
| 2007/0123788 A1 | 5/2007 | Gunderson et al. |
| 2007/0123789 A1 | 5/2007 | Gunderson et al. |

(56) References Cited

U.S. PATENT DOCUMENTS

| | | |
|---|---|---|
| 2007/0123790 A1 | 5/2007 | Gunderson et al. |
| 2007/0123941 A1 | 5/2007 | Gunderson et al. |
| 2007/0135863 A1 | 6/2007 | Gunderson et al. |
| 2007/0135864 A1 | 6/2007 | Gunderson et al. |
| 2007/0167986 A1 | 7/2007 | Gunderson et al. |
| 2008/0065165 A1 | 3/2008 | Johnson |
| 2008/0082012 A1 | 4/2008 | Gunderson et al. |
| 2008/0161872 A1 | 7/2008 | Gunderson |
| 2008/0270036 A1 | 10/2008 | Webb et al. |
| 2010/0280841 A1 | 11/2010 | Dong et al. |
| 2011/0112417 A1 | 5/2011 | Gunderson et al. |

OTHER PUBLICATIONS (PCT/US2012/056987) PCT Notification of Transmittal of the International Search Report and the Written Opinion of the International Searching Authority.

Response to Office Action mailed Mar. 13, 2013, from U.S. Appl. No. 13/250,515, filed Jul. 15, 2013, 17 pp.

Final Office Action from U.S. Appl. No. 13/250,515, mailed Oct. 22, 2013, 8 pages.

U.S. Appl. No. 12/837,320, by Hendrikus A. Westendorp, filed Jul. 15, 2010.

U.S. Appl. No. 13/250,515, by Bruce Gunderson, filed Sep. 30, 2011.

* cited by examiner

ELECTROGRAM SUMMARY

TECHNICAL FIELD

The invention relates to an electrogram (EGM) summary generated by an external computing device based on information retrieved from an implantable medical device (IMD).

BACKGROUND

The capacity of various types of IMDs to collect and store large amounts of physiological data is increasing. Some IMDs implement pre-programmed algorithms to process collected physiological data to, for example, diagnose certain patient conditions and/or guide therapy delivered by the IMD. Some IMDs, such as implantable pacemaker-cardioverter-defibrillators, may implement algorithms to detect and classify cardiac arrhythmia episodes, in response to which the IMD may deliver therapy, such as a defibrillation shock.

IMDs may also implement one or more algorithms to monitor device integrity by, for example, tracking events characteristic of physiological sensing issues and/or device impedance changes. Certain components of implantable medical devices, like any other man-made device, are subject to fault or failure, for example, either due to operator error at the time of implant, or due to normal "wear and tear" on the components during the life of the device. These faults or failures can result in artifact signals which are sensed by the IMD and mistaken for physiological signals, thereby impacting the accuracy of the data analysis performed by the IMD in classifying episodes.

Many sophisticated data processing algorithms have been developed to perform more detailed analyses of data collected by IMDs. Some of these algorithms have been programmed on an external medical device that can be wirelessly coupled, for example, via telemetry, to an IMD for the transfer of the data from the IMD to the external device. Alternately, some of the algorithms have been programmed on computers, which are not wirelessly coupled to the device, and the data is transferred from external medical devices to the computers, for example personal or lap top computers, on a disk or via a network.

Such external algorithms can process the data received from IMDs to come to some conclusions regarding episode classification and events indicative of device integrity issues, and may further provide a presentation of the data in a format that allows a physician or clinician to further analyze the data. Such auxiliary analyses of data transferred from an IMD can bring to light device integrity issues and/or errors in one or more analyses performed by the IMD that have led to misclassification of episodes detected by the IMD. Such auxiliary analysis may thus help an attending physician or other clinician in making decisions to reposition or replace certain portions/components of the device due to faults or failures detected by the auxiliary analysis, and/or in making decisions related to re-programming of the implanted device in order to prevent misclassification errors in the future.

Methods employed by an algorithm for post processing of data associated with arrhythmic episodes, which are detected and classified by an implantable cardioverter defibrillator (ICD), are described in commonly assigned U.S. Pat. No. 7,894,883, entitled METHOD AND APPARATUS FOR POST-PROCESSING OF EPISODE DETECTED BY A MEDICAL DEVICE, incorporated herein by reference in its entirety. Examples of methods employed by algorithms that are tailored to identify and classify events indicative of a device integrity issue, in particular, faults or failures associated with lead components of the device, are described in commonly assigned U.S. Pat. No. 7,539,540, entitled TROUBLESHOOTING METHODS FOR A MEDICAL SYSTEM INCLUDING IMPLANTABLE COMPONENTS and in U.S. Pat. No. 7,047,083, entitled METHOD AND APPARATUS FOR IDENTIFYING LEAD-RELATED CONDITIONS USING LEAD IMPEDANCE MEASUREMENTS which are each hereby incorporated by reference in their entireties.

SUMMARY

In general, the disclosure describes techniques for generating and displaying an EGM summary for use by physicians or other clinicians. An implantable medical device (IMD) transmits EGM signal data for a number of cardiac episodes to an external computing device. The external computing device automatically selects a subset of the cardiac episodes for which information or images are displayed to the user.

In one example, a method comprises receiving cardiac electrogram (EGM) signal data from an implantable medical device (IMD), the EGM signal data including a plurality of detected cardiac episodes, each of the plurality of cardiac episodes classified by the IMD as at least one of a ventricular tachycardia/ventricular fibrillation (VT/VF) episode, a supraventricular tachycardia (SVT) episode, a ventricular tachycardia non-sustained (VTNS) episode, an atrial tachycardia/atrial fibrillation (AT/AF) episode, a monitored VT episode, or a ventricular oversensing (VOS) episode. The method further comprises conducting a retrospective analysis of each of the plurality of cardiac episodes, the retrospective analysis providing a retrospective analysis classification, and selecting, using a processor, a subset of the plurality of cardiac episodes for display based at least in part on at least one of the IMD classification and the retrospective analysis classification, wherein for each episode category including at least one episode, the subset includes greater than or equal to one episode and less than or equal to a predetermined number of episodes.

In another example, the disclosure is directed to a system comprising a communication module configured to receive electrogram (EGM) signal data from an implantable medical device, the EGM signal data including a plurality of cardiac episodes, each of the plurality of each of the plurality of cardiac episodes classified by the implantable medical device as at least one of a ventricular tachycardia/ventricular fibrillation (VT/VF) episode, a supraventricular tachycardia (SVT) episode, a ventricular tachycardia no stimulation (VTNS) episode, an atrial tachycardia/atrial fibrillation (AT/AF) episode, a monitored VT episode, or a ventricular oversensing (VOS) episode, a processor configured to conduct a retrospective analysis for each of the plurality of cardiac episodes, the retrospective analysis providing a retrospective analysis classification, and select a subset of the plurality of cardiac episodes for display based at least in part on at least one of the implantable medical device classification and the retrospective analysis classification, wherein for each episode category including at least one episode, the subset includes greater than or equal to one episode and less than or equal to a predetermined number of episodes. The system further comprises a graphical user interface configured to display a summary of the selected subset of the plurality of cardiac episodes.

In another example, the disclosure is directed to a computer-readable medium containing instructions. The instructions cause a programmable processor to receive cardiac electrogram (EGM) signal data from an implantable medical device (IMD), the EGM signal data including a plurality of detected cardiac episodes, each of the plurality of cardiac episodes classified by the IMD as at least one of a ventricular tachycardia/ventricular fibrillation (VT/VF) episode, a supraventricular tachycardia (SVT) episode, a ventricular tachycardia non-sustained (VTNS) episode, an atrial tachycardia/atrial fibrillation (AT/AF) episode, a monitored VT episode, or a ventricular oversensing (VOS) episode, conduct a retrospective analysis of each of the plurality of cardiac episodes, the retrospective analysis providing a retrospective analysis classification, and select a subset of the plurality of cardiac episodes for display based at least in part on at least one of the IMD classification and the retrospective analysis classification, wherein for each episode category including at least one episode, the subset includes greater than or equal to one episode and less than or equal to a predetermined number of episodes.

In another examples, the disclosure is directed to a system comprising means for receiving cardiac electrogram (EGM) signal data from an implantable medical device (IMD), the EGM signal data including a plurality of detected cardiac episodes, each of the plurality of cardiac episodes classified by the IMD as at least one of a ventricular tachycardia/ventricular fibrillation (VT/VF) episode, a supraventricular tachycardia (SVT) episode, a ventricular tachycardia non-sustained (VTNS) episode, an atrial tachycardia/atrial fibrillation (AT/AF) episode, a monitored VT episode, or a ventricular oversensing (VOS) episode, means for conducting a retrospective analysis of each of the plurality of cardiac episodes, the retrospective analysis providing a retrospective analysis classification, and means for selecting, using a processor, a subset of the plurality of cardiac episodes for display based at least in part on at least one of the IMD classification and the retrospective analysis classification, wherein for each episode category including at least one episode, the subset includes greater than or equal to one episode and less than or equal to a predetermined number of episodes.

The details of one or more examples are set forth in the accompanying drawings and the description below. Other features, objects, and advantages will be apparent from the description and drawings, and from the claims.

DETAILED DESCRIPTION

Figure 1:
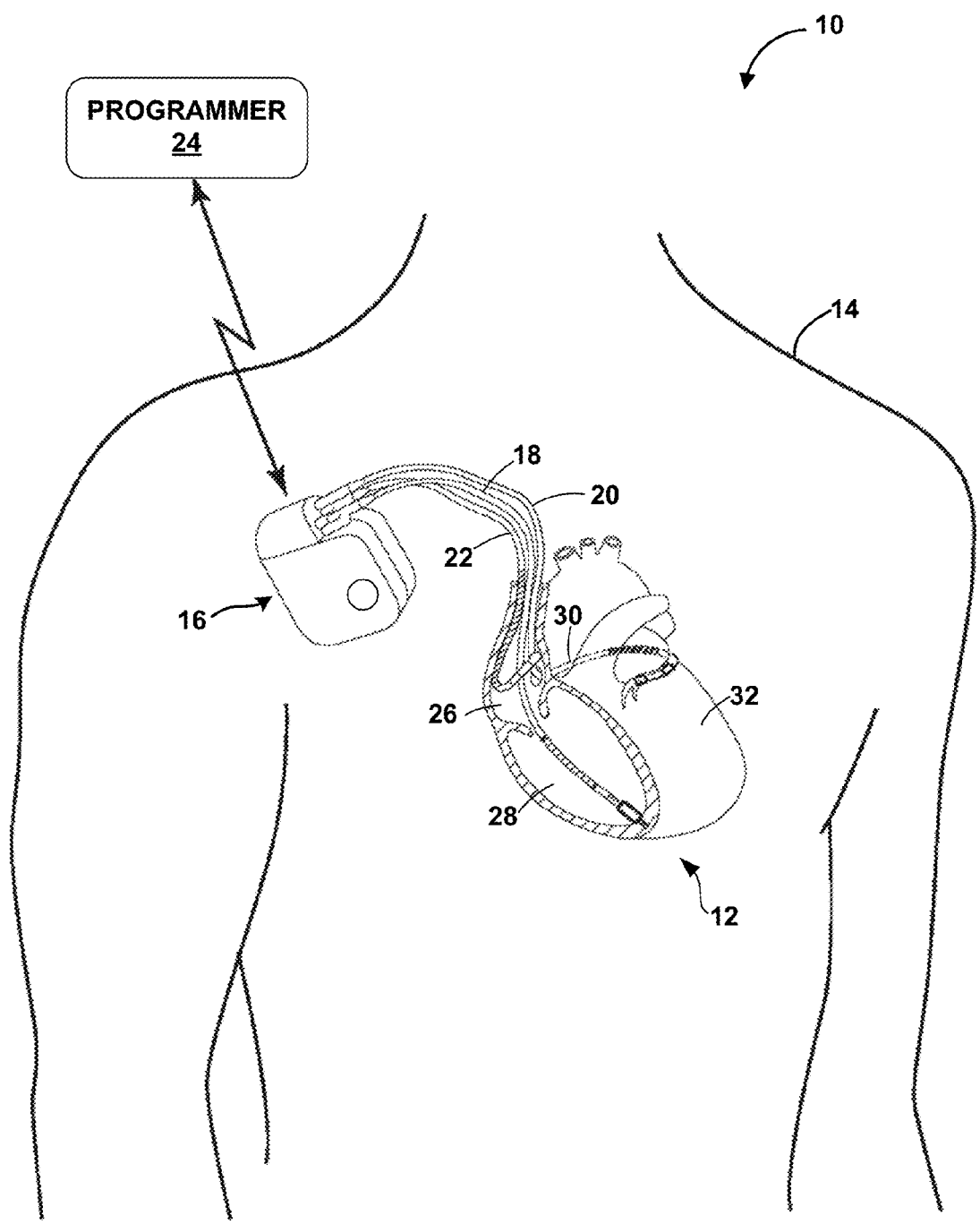
FIG. 1 is a conceptual diagram illustrating an example system for monitoring and treating cardiac episodes and providing a summary of the episodes.

The present disclosure is directed to techniques for automatically generating summary for display to a user, such as a physician or clinician. An IMD transmits information regarding a plurality of cardiac episodes identified by the IMD to an external computing device. The external computing device selects a subset of the cardiac episodes to be presented to the user. The selection may be based on a set of priority rules. In some examples the priority rules are set, at least in part, based on input from the user. The number of cardiac episodes selected may be based on a default number to limit the amount of information presented to the user. In other examples, the number may be customizable by the user.

Information transmitted by an IMD to an external computing device may include EGM data, marker channel data, classification of a cardiac episode by the IMD, treatment provided, and time and date of the cardiac episode, for example. The information provided by the IMD may be used by the external computing device to select episodes for inclusion in an EGM summary presented to a user based on a set of priority rules.

The priority rules may include using information provided by the IMD to sort the episodes based on the classification provided by the IMD. The episode classifications may include, for example, ventricular tachycardia/ventricular fibrillation (VT/VF) episodes in which a shock was delivered by the IMD, supraventricular tachycardia (SVT) episodes, monitored VT episodes, non-sustained VT (VTNS) episodes, atrial tachycardia/atrial fibrillation (AT/AF) episodes, ventricular oversensing (VOS) episodes, symptomatic episodes, ventricular sense episodes, and bradycardia episodes.

A computing device or other external device may select episodes from each of the episode types. In some examples, the same number of episodes may be selected from each category. In other examples, certain categories may be given priority and more example episodes may be selected from the prioritized categories. For example, a greater number of VT/VF episodes may be presented than SVT episodes.

In selecting VT/VF episodes, an external device may consider information including, for example, regularity of ventricular or atrial rate, the number of shocks delivered to a patient during a given episode, the number of anti-tachycardia pacing (ATP) pulse trains delivered for a given episode, whether or not acceleration occurred in episodes requiring ATP, severity of treatment, or the timing of the episode. An external device may also select VT/VF episodes based on length of the episode, average ventricular or atrial cycle length, or the atrial sensed event rate relative to the ventricular sensed event rate during the episode. In some examples, the external device may select individual episodes based on the presence of unique interval morphologies, or where it is determined that a particular chamber is leading the rhythm.

In instances where an external device provides retrospective analysis for the cardiac episodes transmitted from an IMD, the external device may select episodes based on inability of an external device to classify the episode, algorithm classification result, algorithm classification confidence, classification rationale, conflict between classification by the external device and the IMD, or conflict between a clinician's opinion and the classification or either the external device or the IMD.

Selection of SVT episodes for inclusion in an EGM summary may be made based on duration, reason for withholding treatment, ventricular interval length, or timing of the episodes, for example. Representative SVT episodes may also be selected based on morphology of sensed R-waves during the episode. In some examples, the SVT episodes may be annotated with the primary reason for withholding treatment. If included in the EGM summary, the annotation may appear next to a thumbnail of an EGM signal for the cardiac episode, for example.

Selection of monitored VT episodes may be based on the timing of the cardiac episode or characteristics of the episode. For example, episodes may be selected based on including an average ventricular rate during the episode significantly different than that of other monitored VT episodes, including an average atrial rate during the episode significantly different atrial rates than that of other monitored VT episodes, having the fastest ventricular rate amongst monitored VT episodes, or the duration of the cardiac episode. Representative monitored VT episodes may be selected for inclusion in an EGM summary based on retrospective analysis cardiac episode classification. In some examples, a monitored VT episode has cycle length of between 340 ms and 400 ms. A monitored VT episode is not treated unless the cycle length changes, falling within a treatable zone. In some examples the treatable zone may be a cycle length of less than 340 ms.

Non-sustained VT (VTNS) episodes may be selected for inclusion in an EGM summary based on which episodes are most recent, the length of the episode, or cycle length within the episode. VTNS episodes may also be selected in a manner to show representative episodes for similar algorithm classifications provided during retrospective analysis. In some examples VTNS episode is an episode with cycle length within a treatable range lasting longer than a first predetermined number of episodes bust less than the NID. For example, an episode with a cycle length less than 340 ms for the last 10 beats may be considered VTNS. However, if the cycle length stays below 340 for 18 beats (NID), then the episode may be detected as VT/VF.

AT/AF episodes may be selected for inclusion in an EGM summary report based on when the episode occurred, duration of the episode, ventricular rate during the episode, or degree of A-A interval regularity during the episode, for example. AT/AF episodes may also be selected to provide representative episodes with or without far-field R-waves, or based on a specific algorithm classification or reasoning provided by a retrospective analysis.

VOS episodes may be selected for inclusion in an EGM summary report based on when the episode, occurred, duration of the episode, severity of the VOS issue, or amount of lead noise present, for example. VOS episodes may also be selected based on a retrospective analysis classification or reasoning provided by the retrospective analysis for the determination of VOS.

Symptomatic episodes may be stored by an IMD based on user initiation. In some examples, a user may feel a symptom, such as dizziness, and use a patient programmer to initiate storage of an episode by the IMD. Symptomatic episodes may be selected for inclusion in an EGM summary based on patient symptoms at time of storage, for example.

Ventricular sense episodes may be stored by an IMD in response to pacing. In some examples, a ventricular sense episode may only include a marker channel, and not an EGM signal. Ventricular sense episodes may be selected for inclusion in an EGM summary based on duration of the episode, when the episode occurred or ventricular rate during the episode, for example.

Bradycardia episodes may be stored in response to a slow heart rate. In some examples, bradycardia episodes may be selected for inclusion in an EGM summary based on duration of the episode or heart rate during the episode.

The various cardiac episodes selected for inclusion within the EGM summary may be prioritized in order to present the cardiac episodes that are most likely to be of interest to a clinician or physician first. In some examples, a physician or other user may provide priority preferences. The preferences provided by the physician or other user may apply to all patients considered by that user, or the user may provide patient- or class-specific preferences. For example, EGM summaries for patients with a particular condition or diagnosis may present certain cardiac episodes higher in the EGM summary. A default prioritization scheme may show treated VT/VF episodes first, followed by monitored VT episodes, VTNS episodes, SVT episodes, AT/AF episodes and VOS episodes.

Cardiac episodes presented in an EGM summary may also be prioritized within each classification type. For example, the episodes may be shown in chronological or reverse chronological order. Treated VT/VF episodes may be prioritized by severity of treatment, for example. In some examples, VT/VF episodes with failed treatments may be presented first. In some examples, episodes may also be displayed in order based on algorithm classification confidence. IMD 16 may include a classification confidence level along with the initial classification of the cardiac episode. Classification confidence may be displayed as part of the EGM summary numerically, as a discrete rating, i.e., high or low, or with a confidence meter. The reasons for classification may also be prioritized. For example, whether IMD made the classification based on relative atrial and ventricular rates, or based on morphology matching. The reason used for prioritization may be from the initial classification by IMD 16 or from the classification during retrospective analysis by processor 106.

The cardiac episodes selected for inclusion within an EGM summary report may be presented to a user in a variety of manners. A thumbnail of an EGM snippet may be presented for each episode. In some examples, additional information, including the classification of the episode by the IMD, the classification of the episode made by a retrospective analysis performed by an external computer, or classification may be a physician or clinician, via an electronic medical record (EMR), for example, may also be presented. Comments regarding why a particular classification was made by the IMD, clinician, or the external computer may also be included. In some examples, an interval plot may be presented in the EGM summary page. An interval plot, as described in more detail below, graphically illustrates the length of each interval during a cardiac episode in chronological order. Information regarding treatment delivered by the IMD in response to the episode, as well as the length of the episode or the confidence of the classification by the external computer may also be presented. In other examples, information or annotations regarding classification may be presented with or without an image of the EGM signal or the interval plot.

Automatic classification results from retrospective analysis, if available, may be displayed along with each selected cardiac episode. Various labels may be used including "SVT", "VOS", "VT/VF", "inappropriate" (meaning, "algorithm conflicts with device classification") or "appropriate" (meaning, "algorithm confirms device classification"), for example.

External algorithm-determined labels of particular episode characteristics may also be displayed. For example, characteristics such as sudden onset, morphology change, a morphology matching a particular template, an indication of other episodes including similar morphology or an indication that the external algorithm was unable to determine the appropriate classification.

An EGM summary report may also provide information regarding whether there are other cardiac episodes, not displayed, that are similar to episodes that have been included in the EGM summary. For example, the EGM summary may include a note that a representative EGM signal is one of five VT/VF episodes with sudden onset and a single ATP terminated, or the number of particular episodes, not shown, with similar sensed R-wave morphology, for example. In some examples, the EGM summary report may provide information regarding whether a cardiac episode in the current transmission has characteristics similar to one or more episodes from previous transmissions.

An EGM summary report may allow a user to select a cardiac episode for more careful review. In some examples, when a particular cardiac episode is selected, a larger, more detailed image of the EGM signal may be presented to the user. However, even when a more detailed image is presented, only a portion of the episode may be viewed at a time. Accordingly, a portion of the full EGM signal may be selected to be shown in an EGM snippet. An EGM snippet may be a portion of an EGM signal of a predetermined length, shorter than the entire cardiac episode.

A default portion of the EGM signal may be selected for initial presentation to the user. The section may be a portion of the EGM signal just prior to detection (right aligned with detection at the end) or the section may be at the beginning of the EGM signal storage (left-aligned with the first EGM beat stored by the IMD for the episode), for example. In some examples, logic may be used to determine onset of the episode, and the portion of EGM signal stored by the IMD for the episode that is presented by the external computing device may include episode onset. Onset may be determined by counting backwards from detection by the number of interval determination (NID) employed by the IMD to detect the episode, by working backwards from detection to find an abrupt change in interval length, or by identifying the first of several slow intervals, as examples.

In examples where retrospective analysis is used, the portion of the EGM signal used by the arrhythmia analyzer algorithm to make its final classification decision may be selected for display to a user or for inclusion in an EGM summary. An EGM snippet may display the EGM signal during and after ATP, a portion of the EGM signal with oversensing, or a portion with a ventricular morphology change, for example. The portion of the EGM signal displayed may be different if pre-storage is on or off. An IMD may use pre-storage to store a portion of an EGM signal of a predetermined length that is continuously updated and overwritten over time. The portion of the EGM signal stored in pre-storage may be stored to long term memory upon the occurrence of one or more predetermined events. This may allow for an EGM signal associated with a cardiac episode to include a greater number of episodes of interest for display to a user once transmitted to an external computing device. Without pre-storage a user may not be able to evaluate how quickly an IMD detected the possibility of an arrhythmia. The user may be unable to evaluate the events prior to detection, or onset of storage of the arrhythmia. Without pre-storage the EGM signal associated with the cardiac episode may only include beats occurring after a predetermined event triggers storage of the EGM signal.

Consistent with the present disclosure, the portion of the EGM signal displayed may also be dynamically changed by a user. A user may be able to manipulate a window on an interval plot to change which portion of the EGM signal and/or the marker channel are displayed. In some examples the EGM signal and marker channel show separate parts of the EGM signal. A user may, for example, place a marker channel window to encompass the onset of the cardiac episode, while placing an EGM signal window to show the portion of the EGM signal immediately preceding detection by the IMD.

The EGM display may include information or annotations in addition to the EGM signal and the marker channel. A marker channel tail may also be displayed and is a portion of the marker channel in addition to the portion of the marker channel that aligns with the portion of the EGM signal displayed. In some examples, an IMD may store more marker channel prior to detection of a cardiac episode than EGM signal; this additional marker channel information may be the marker channel tail. In some examples, a larger portion of the marker channel may be displayed, regardless of the amount of EGM signal stored. Retrospective analysis may determine whether undersensed or oversensed beats are present and these beats may be delineated on the EGM display. For example, a special marker, color, annotation, or demarcation may be used. Other annotation on an interval plot, EGM snippet or marker channel may be based on other specifics from the retrospective analysis including, for example, "morphology change detected here," "abrupt change in interval length," or "this morphology matches that of episode #32." In addition, a user may be able to select which EGM signal to display, such as ventricular near-field, ventricular far-field, or atrial.

The EGM display may also include episode information such as the episode number, date and time of the cardiac episode, the IMD's detected classification, the duration of the episode, cycle lengths (e.g., R-R or P-P) during the episode, or wavelet percentage match, for example. A wavelet percentage match may be the percentage of beats, or wavelets, within an episode that match a template wavelet or beat. The amount and type of information presented may be customizable based on user preference. The EGM display may also allow for a user to manually enter comments via keyboard, for example. In some examples, comments may be manually entered into another system such as an EMR and added to the display for the EGM summary report.

An interval plot thumbnail may also be presented to a user along with an EGM snippet for a chosen cardiac episode. Through the interval plot thumbnail, an interval plot may be displayed in a compressed manner with labels for detection, ATP, shocks, or termination. The y-axis range may be auto adjusting, display a fixed range, or be customizable for each individual plot. The y-axis range may also be customizable based on user preference. In some examples, the interval plot may include one or more windows that indicate which portion of the EGM signal and marker channel are being displayed. The windows may surround a portion of the interval plot that corresponds to the portion of the EGM signal and marker channel being displayed.

An EGM summary or a display of a single EGM signal may also include a reference EGM signal. The reference EGM signal may be a recent EGM signal that was collected at the time of transmission from the implantable medical device to the external computing device. In some examples, if the patient's heart rhythm is mostly paced, the IMD may attempt to collect an EGM of the underlying rhythm by temporarily suspending pacing during collection of the EGM. In examples where the pacing provided to the patient by the IMD is cardiac resynchronization therapy, the interval between atrial beats and ventricular beats may be extended in an attempt to expose and collect the underlying ventricular rhythm. In some examples, an arrhythmia analyzer algorithm may be used to determine and display undersensed or oversensed beats within the reference EGM. The view of the reference EGM may be displayed with or without the post-processing analysis of the reference EGM.

An EGM summary report may also include a timeline of cardiac episodes transmitted from an IMD to an external computing device. The timeline may be a graph showing the episode occurrences by type and date. In some examples, the timeline may include episodes from the most recent transmission. In some examples, the timeline may include episodes from more than one transmission. In some examples, the graph may also include the average cycle length for each episode in the graph. In some examples, a graphical time line may show episode by classification by retrospective analysis. In other examples, the graphical timeline may show episode characteristics. The graphical timeline may also show programming suggestions, such as an automatically proposed value for the tachycardia detection interval (TDI) based on algorithm classification.

An EGM summary report according to the present disclosure may include one or more of the features described in more detail below. In general the EGM summary report automatically displays information about a plurality of cardiac episodes transmitted by an IMD to a user in a more concise and easy to use manner than a simple printout of the information provided by the IMD.

FIG. 1 is a conceptual diagram illustrating an example system 10 for monitoring and treating cardiac episodes and providing a summary of the episodes over a predetermined time period to a user, such as a physician. As illustrated in FIG. 1, a system for monitoring and treating cardiac episodes and providing a summary of the episodes to a user includes an implantable medical device (IMD) 16, such as an implantable cardiac pacemaker, implantable cardioverter/defibrillator (ICD), or pacemaker/cardioverter/defibrillator, for example. IMD 16 is connected to leads 18, 20 and 22 and is communicatively coupled to a programmer 24. IMD 16 senses electrical signal attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses. IMD 16 may monitor EGM signals collected by electrodes on leads 18, 20 or 22, and based on the EGM signal detect and treat cardiac episodes. Programmer 24 may receive and summarize the EGM signal based on the detection and treatment of cardiac episodes provided by IMD 16. The system for summarizing and displaying information regarding diagnosis and treatment may also be used with other medical devices, such as a cardiomyostimulator, a drug delivery system, cardiac and other physiological monitors, electrical stimulators including nerve, muscle and deep brain stimulators, cochlear implants and heart assist IMDs or pumps, for example.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. Programmer 24 may provide to the user a summary of physiological and diagnostic information for patient 12 over a period of time. A user may also interact with programmer 24 to program IMD 16, e.g., select values for operational parameters of the IMD. Programmer 24 may include a processor configured to evaluate EGM signals transmitted from IMD 16 to programmer 24. In some examples, programmer 24 may evaluate a prior classification of an episode by IMD 16.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

In some examples, data acquired by IMD 16 can be monitored by an external system, which may comprise the programmer 24. The retrospective analysis of cardiac episodes according to an example of the present disclosure may take place in the programmer 24 once the required data is transmitted from IMD 16 to the programmer 24. In some examples, programmer 24 (or another device capable of communicating with IMD 16) may transmit the required data to another external device, not shown in FIG. 1, for processing, analysis and presentation to a user.

Figure 2:
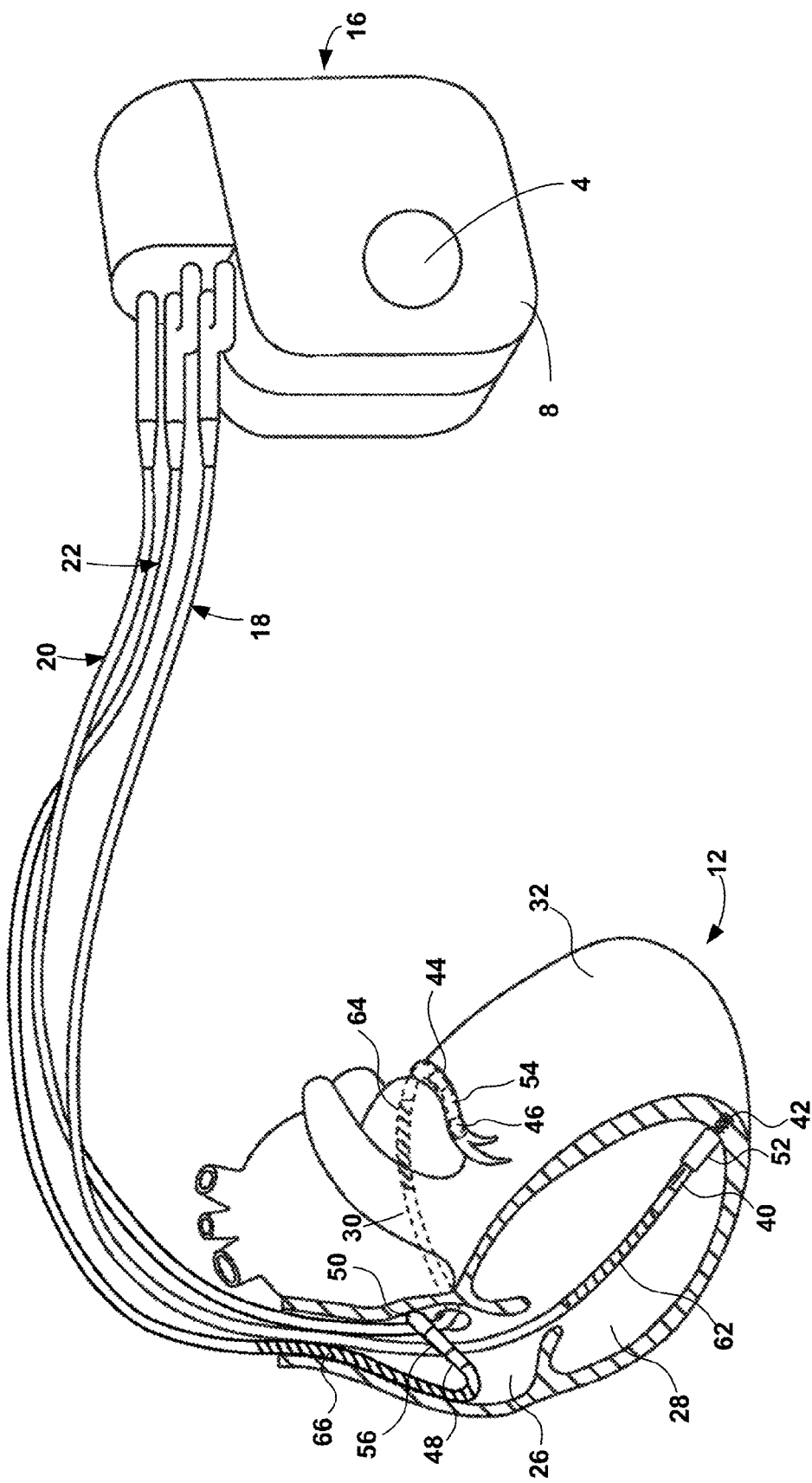
FIG. 2 is a conceptual diagram illustrating the implantable medical device of FIG. 1.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a memory for storing the sensed electrical signals. Housing 8 may also enclose a telemetry module for communication between IMD 16 and programmer 24.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart.

Figure 3:
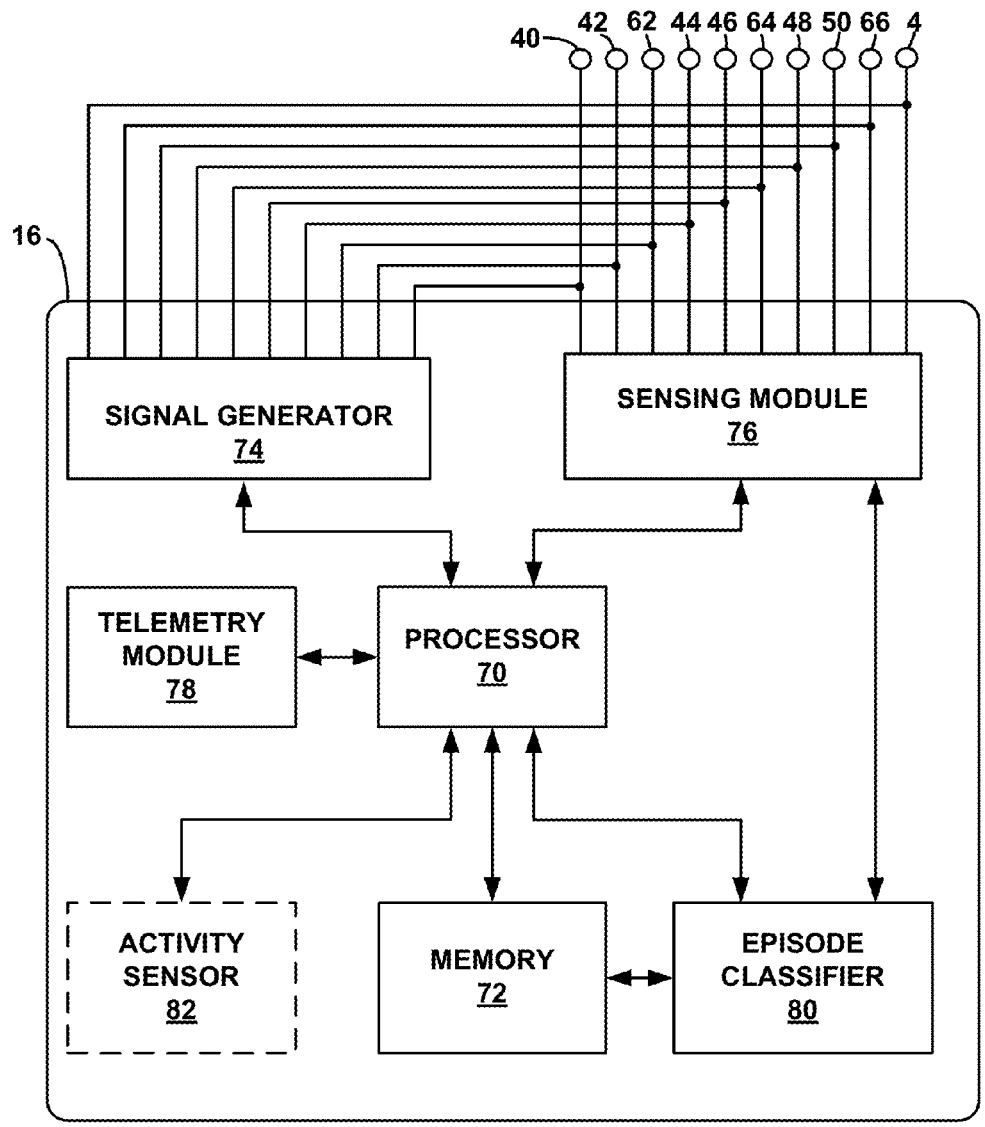
FIG. 3 is a block diagram illustrating an example IMD that monitors EGM signals.

FIG. 3 is a block diagram illustrating an example IMD 16 that monitors EGM signals and classifies abnormal signals before providing a therapeutic response. In the illustrated example, IMD 16 includes a processor 70, memory 72, signal generator 74, sensing module 76, telemetry module 78, episode classifier 80, and activity sensor 82. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with amplitudes, pulse widths, frequency, or electrode polarities specified by the selected one or more therapy programs or parameters. Processor 70 may modify or initiate the electrical pulses delivered by signal generator 75 based on a detection or classification of an EGM signal by episode classifier 80.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70 or episode classifier 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM. In order to learn more about when IMD 16 is misclassifying patient's heart rhythms as shockable episodes, processor 70 may send a portion of an EGM signal that resulted in a classification of a treatable tachyarrhythmia.

IMD 16 also includes episode classifier 80. In some examples, classification of a patient's heart rhythm based on an EGM signal form sensing module 76 occurs in episode classifier 80. Episode classifier may employ any of the methods described herein for identifying a tachyarrhythmia from an ongoing EGM signal. In some examples, episode classifier 80 stores a portion of the EGM signal within memory 72 on an ongoing basis. When a tachyarrhythmia is not detected by the episode classifier, the EGM signal may be written over after a period of time. In response to a tachyarrhythmia being detected, episode classifier 80 may direct memory 72 to store on a long term basis a time period or portion of the EGM signal leading up to the detection of the tachyarrhythmia, along with the specific classification, e.g., VT, VF, or SVT. In some examples, detection may not result in stimulation being provided by IMD 16. The corresponding EGM signal may be categorized as VTNS, AT, AF, monitored VT, or a VOS episode.

Although processor 70 and episode classifier 80 are illustrated as separate modules in FIG. 3, processor 70 and episode classifier 80 may be incorporated in a single processing unit. Episode classifier 80 may be a component of or a module executed by processor 70.

Activity sensor 82 may be optionally included in some examples of IMD 16. Activity sensor 82 may include one or more accelerometers. Information obtained from activity sensor 82 may be used to determine activity level or posture leading up to, or at the time of the abnormal heart rhythm. In some examples, this information may be used by IMD 16, e.g., episode classifier 80, to aid in the classification of an abnormal heart rhythm.

Activity sensor 82 may, for example, take the form of one or more accelerometers, or any other sensor known in the art for detecting activity, e.g., body movements or footfalls, or posture. In some examples, activity sensor 82 may comprise a three-axis accelerometer. Processor 70 may determine an activity level count at regular intervals based on the signal(s) from activity sensor 82. In some examples, processor 70 may determine a running average activity count based on the information provided by activity sensor 82. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 82 may be located outside of the housing 8 of IMD 16. Activity sensor 82 may be located on a lead that is coupled to IMD 16 or may be implemented in a remote sensor that wirelessly communicates with IMD 16 via telemetry module 78. In any case, activity sensor 82 is electrically or wirelessly coupled to circuitry contained within housing 8 of IMD 16.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals selected by episode classifier 80 to programmer 24. Processor 70 may also generate and store marker codes indicative of different cardiac or other physiological events detected by sensing module 76 or episode classifier 80, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 4:
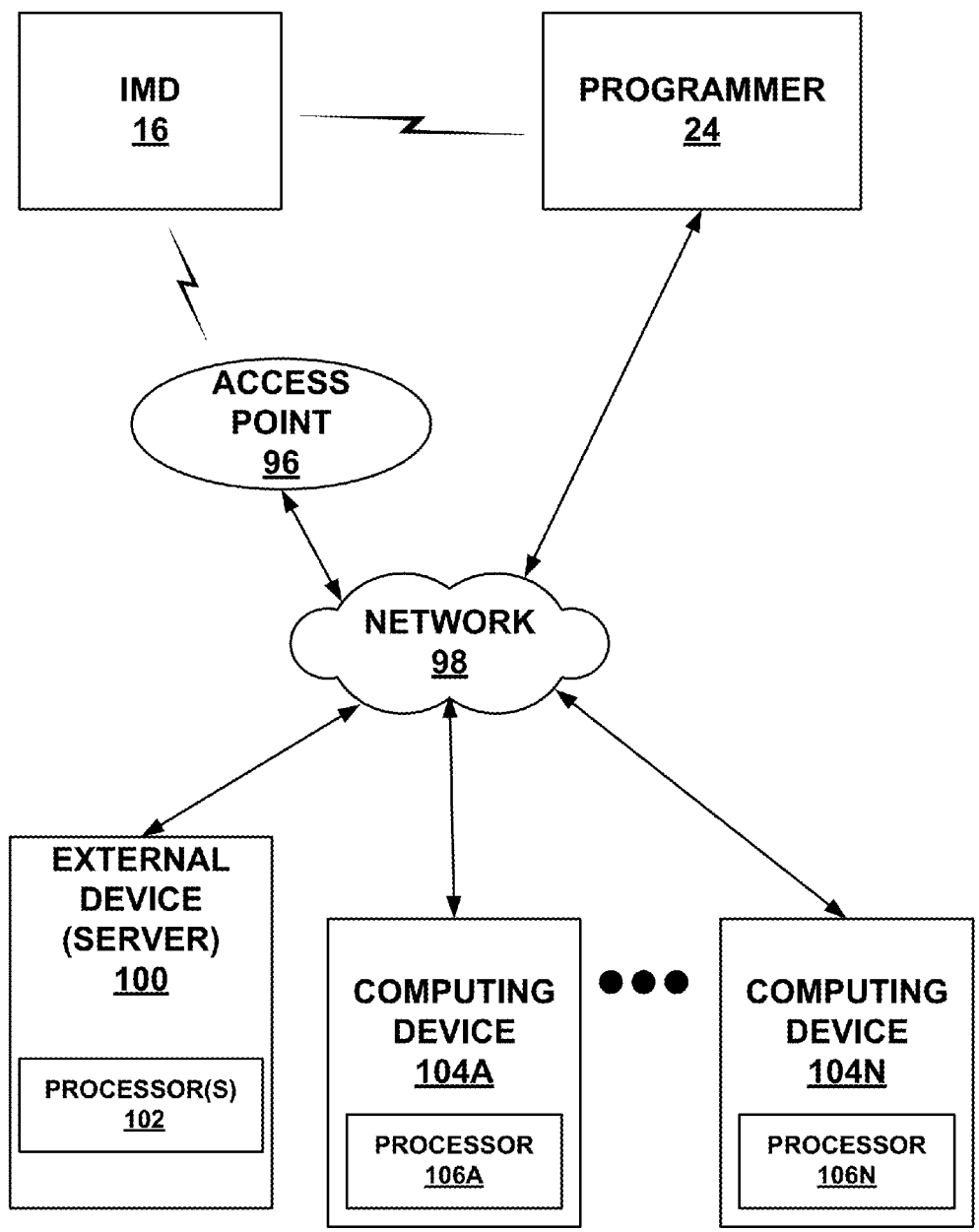
FIG. 4 is a block diagram illustrating an example system that includes an external device, such as a server, and one or more computing device.

FIG. 4 is a block diagram illustrating an example system that includes an external device, such as a server 100, and one or more computing devices 104A-104N that are coupled to the IMD 16 and programmer 24 shown in FIG. 1 via a network 98. Network 98 may be generally used to transmit detection or diagnostic information (e.g., detection by IMD 16 of an abnormal EGM signal) from an IMD 16 to a remote external computing device. In some examples, EGM signals may be transmitted to an external device for display to a user. In some examples, the EGM signal is subjected to retrospective analysis by the external device.

In some examples, the information transmitted by IMD 16 may allow a clinician or other healthcare professional to monitor patient 14 remotely. In some examples, IMD 16 may use a telemetry module to communicate with programmer 24 via a first wireless connection, and to communicate with access point 96 via a second wireless connection, e.g., at different times. In the example of FIG. 4, access point 96, programmer 24, server 100 and computing devices 104A-104N are interconnected, and able to communicate with each other through network 98. In some cases, one or more of access point 96, programmer 24, server 100 and computing devices 104A-104N may be coupled to network 98 via one or more wireless connections. IMD 16, programmer 24, server 100, and computing devices 104A-104N may each comprise one or more processors, such as one or more microprocessors, DSPs, ASICs, FPGAs, programmable logic circuitry, or the like, that may perform various functions and operations, such as those described herein.

Access point 96 may comprise a device that connects to network 98 via any of a variety of connections, such as telephone dial-up, digital subscriber line (DSL), or cable modem connections. In other examples, access point 96 may be coupled to network 98 through different forms of connections, including wired or wireless connections. In some examples, access point 96 may be co-located with patient 14 and may comprise one or more programming units and/or computing devices (e.g., one or more monitoring units) that may perform various functions and operations described herein. For example, access point 96 may include a home-monitoring unit that is co-located with patient 14 and that may monitor the activity of IMD 16. In some examples, server 100 or computing devices 104 may control or perform any of the various functions or operations described herein, e.g., determine, based on EGM signal data, whether IMD 16 properly classified various cardiac episodes, and displaying a summary of the EGM signal data transmitted by IMD 16.

In some cases, server 100 may be configured to provide a secure storage site for archival of diagnostic information (e.g., occurrence of detection and shock by IMD 16 and attendant circumstances such as the EGM signal leading up to detection) that has been collected and generated from IMD 16 and/or programmer 24. Network 98 may comprise a local area network, wide area network, or global network, such as the Internet. In some cases, programmer 24 or server 100 may assemble EGM signal and diagnosis information in web pages or other documents for viewing by trained professionals, such as clinicians, via viewing terminals associated with computing devices 104. The system of FIG. 4 may be implemented, in some aspects, with general network technology and functionality similar to that provide by the Medtronic CareLink® Network developed by Medtronic, Inc., of Minneapolis, Minn.

In the example of FIG. 4, external server 100 may receive EGM signal data from IMD 16 via network 204. Based on the EGM signal data received, processor(s) 102 may preform one or more of the functions described with herein with respect to processors 106A-106N of computing devices 104A-104N. Processor(s) 102 may also carry out one or more of the functions described herein with respect to processor 70 of IMD 16. Programmer 24 may also include a processor that performs one or more of the functions described herein with respect to processor 106 of computing device 104. For example, episode classification may be carried out by any of the programmer 24, external server 100 or computing device 104.

Although described below as carried out by computing device 104, in some examples, another device, such as server 100 may perform at least a portion of the method for producing an EGM summary. For example, a physician or clinician my access an EGM summary via computing device 104 including a user interface, but on more of the computing aspects described below for generating the EGM summary may be carried out on external server 100.

Figure 5:
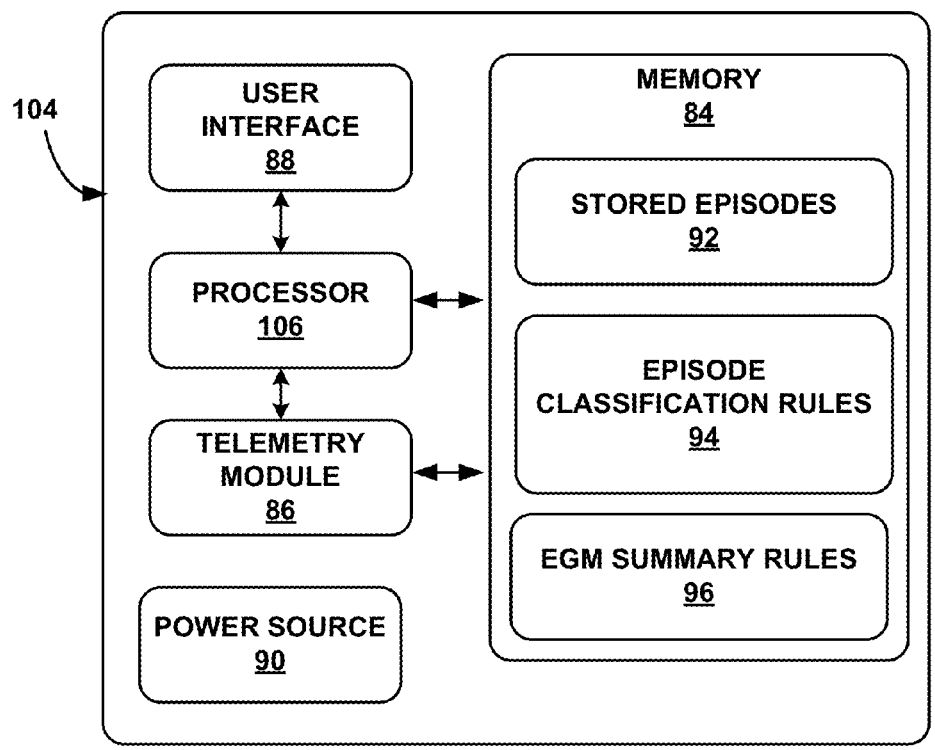
FIG. 5 is a block diagram illustrating an example configuration of the computing device of FIG. 4.

FIG. 5 is a block diagram illustrating an example computing device 104 of FIG. 4. As illustrated in FIG. 5, computing device 104 may include a processor 106, a memory 84, a telemetry module 86, a user interface 86, and a power source 90. Processor 106 stores and retrieves information and instructions to and from memory 84. Processor 106 may include a microprocessor, a microcontroller, a DSP, an ASIC, an FPGA, or other equivalent discrete or integrated logic circuitry. Accordingly, processor 106 may include any suitable structure, whether in hardware, software, firmware or any combination thereof, to perform the functions ascribed herein to processor 106.

Telemetry module 86 receives EGM signal data from IMD 16. In some examples, the EGM Signal data is transmitted from IMD 16 via access point 96 and network 98. The EGM signal data may be transmitted to telemetry module 86 in response to IMD 16 detecting an arrhythmia and responding with electrical stimulation. In some examples, portions of EGM signal data are stored in memory 72 of IMD 16 until a predetermined event occurs. After the event has occurred the data is transmitted via telemetry module 78 of IMD 16 to telemetry module 86 of computing device 104. For example, every three months IMD 16 may transmit EGM signal data selected by episode classifier 80 and stored in memory 72. In some examples telemetry module 86 sends program information to IMD 16, e.g., to program the functionality of IMD 16.

A user, such as a clinician may interact with computing device 104 through user interface 88. The techniques of this disclosure are directed to providing a summary of the EGM signal data transmitted from IMD 16 to computing device 104. In some examples, computing device 104 may provide retrospective analysis of the EGM signal to help a user determine the accuracy of the current classification schemes used by IMD 16.

User interface 88 includes a display (not shown), such as a LCD or LED display or other type of screen, to present information related to the therapy, such as information related to current stimulation parameters and electrode combinations and when configured to allow a physician to review EGM information transmitted from IMD 16, to display a summary of a plurality of cardiac episodes of patient 14. In some examples, the summary may include images of EGM signals associated with cardiac episodes and/or text. In addition, user interface 88 may include an input mechanism to receive input from the user. The input mechanisms may include, for example, buttons, a keypad (e.g., an alphanumeric keypad), a peripheral pointing device, or another input mechanism that allows the user to navigate through user interfaces presented by processor 106 of computing device 104 and provide input. The input may include, for example, selection of one or more cardiac episodes from an EGM summary for further review.

If computing device includes buttons and a keypad, the buttons may be dedicated to performing a certain function, e.g., a power button, or the buttons and the keypad may be soft keys that change in function depending upon the section of the user interface currently viewed by the user. Alternatively, the display (not shown) of computing device 104 may be a touch screen that allows the user to provide input directly to the user interface shown on the display. The user may use a stylus or a finger to provide input to the display. In other examples, user interface 88 also includes audio circuitry for providing audible instructions or sounds to patient 14 and/or receiving voice commands from patient 14, which may be useful if patient 14 has limited motor functions. Patient 14, a clinician, or another user may also interact with computing device 104 to manually select operational parameters, e.g., for cardiac sensing or delivery of therapy, for IMD 16.

Processor 106 receives a segment of EGM signal data containing representing a cardiac episode resulting in detection of an arrhythmia followed by electrical stimulation based on detection and classification. The episode may be received from telemetry module 86 or from memory 84. The episodes received from IMD 16 may be stored in stored episodes 92 of memory 84 until retrieved by processor 106 for classification, summation, or display. Processor 106 may apply episode classification rules stored in episode classification rule 94 to the cardiac episode. Processor 106 may also select stored episodes 92 based on EGM summary rule 96 in order to provide an EGM summary to a user via user interface 88.

As shown in FIG. 5, memory 84 includes stored episodes 92, episode classification rules 94 and EGM summary rules 96 in separate memories within memory 84 or separate areas within memory 84. Memory 84 may also include instructions for operating user interface 88, telemetry module 86, and for managing power source 90. Memory 84 may include any volatile or nonvolatile memory such as RAM, ROM, EEPROM or flash memory. Memory 84 may also include a removable memory portion that may be used to provide memory updates or increases in memory capacities. A removable memory may also allow sensitive patient data to be removed before computing device 104 is used by a different patient.

Stored episodes 92 stores EGM signal data received from IMD 16 via telemetry module 86. In some examples, the EGM signal data is separated into episodes, and each episode is saved along with a diagnosis made by IMD 16 based on the EGM signal data in the episode. IMD 16 may transmit EGM signal data at predetermined time intervals, for example every three months. The EGM signals are received by telemetry module 86 and stored in stored episodes 92. In some examples, processor 106, retrieves episodes stored in stored episodes 92 one at a time and confirms or rejects the diagnosis of IMD 16 using episode classification rules stored in episode classification rule 94. In some examples, a user may select one or more episodes stored in stored episodes 92 for retrospective analysis. Processor 106 may retrieve episodes based on EGM summary rules 96.

Episode classification rules 94 stores one or more classification algorithms or sets of classification rules used by processor 106 to perform retrospective analysis on cardiac episodes transmitted by IMD 16 to computing device 104. In some examples, the episode classification rules classify each episode as SVT, VT/VF, or unknown. In some examples, the classification rules provide comments regarding the rule used to provide the classification. In some examples, the classifications are compared to the detection classification generated by IMD 16 prior to delivery of therapy.

EGM summary rules 96 stores rules that, when implemented by processor 106, result in the selection of a subset of the cardiac episodes in stored episodes 92 for display to a user via user interface 88. In some examples, a user may modify the EGM summary rules 96. In some examples, EGM summary rules 96 may store a set of rules that are specific to a specific patient, specific patient symptoms, or a particular patient diagnosis. For example, patient 14 may relay to a physician that the patient felt and increased number of shocks since the last appointment or last transmission of EGM data. In response to such an indication, the physician may configure EGM summary rules 96, via user interface 88, to include a rule set that puts greater emphasis on VT/VF episodes, for example. The modified rule set may be stored in EGM summary rules 96.

In some examples the EGM summary rules 96 includes directions for categorizing the cardiac episodes, and selecting subset of each category of cardiac episodes. In some examples, the directions include instructions regarding prioritization of the selected cardiac episodes. The directions stored in EGM summary rules 96 may also include instructions on how to determine which portion of a full EGM for the cardiac episode to display, as well as possible characteristics of the EGM snippet to display. The various rules stored in EGM summary rules 96 will be described in more detail below with respect to FIGS. 6-11.

Figure 6:
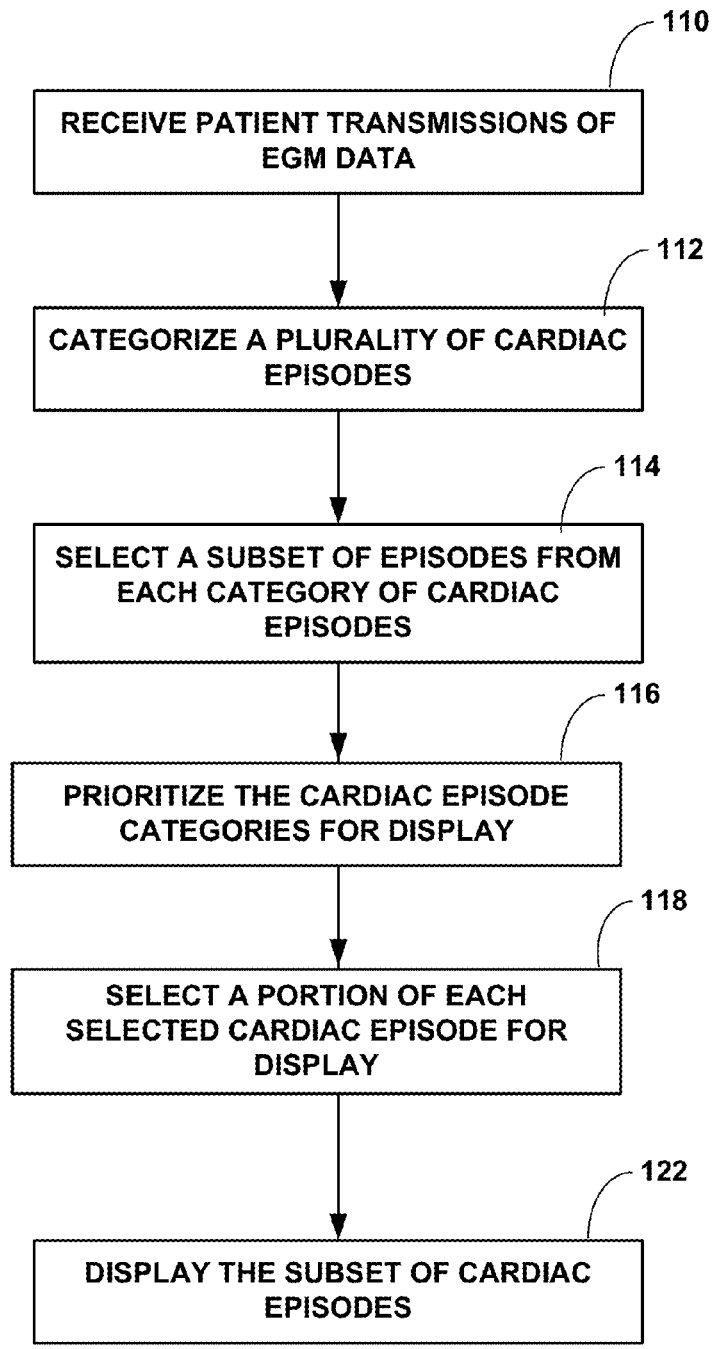
FIG. 6 is a flow diagram illustrating an example method of creating an EGM summary consistent with the present disclosure.

FIG. 6 is a flow chart illustrating an example method of creating an EGM summary consistent with the present disclosure. Although described with respect to computing device 104, one or more of the steps may be carried out by a programmer 24, or external server 100, for example. A computing device 104 receives transmissions of patient EGM data (110), e.g., from IMDs 16. In some examples, a number of IMDs each send EGM data for their respective patients to external device 100. Computing devices 104A-104N may retrieve individual patient transmissions for storage, processing and display. Processor 106 categorizes each of the plurality of cardiac episodes (112) associated with a particular patient. In some examples, the cardiac episodes are categorized based on the detection classification provided by IMD 16. The cardiac episodes may be classified as VT/VF, SVT, monitored VT, VTNS, AT/AF or VOS. In some examples, the cardiac episodes may be further categorized based on the results of retrospective analysis performed by processor 106 to determine whether IMD 16 properly classified each of the episodes. An inappropriate classification may be a result of oversensing, undersensing or lead noise, for example. In some examples, processor 106 may categorize an episode based on why IMD 16 inappropriately classified the episode. In such examples, an additional category may exist for cardiac episode with conflicting classifications.

Processor 106 may select a subset of episodes from each category of cardiac episodes (114) based EGM summary rules 96. The summary rules 96 may include a predetermined number of episodes for selection in each category. The number may be the same for each category, or may vary depending on category. In some examples, the summary rules 96 may include a total number of episodes to be selected, with flexibility regarding how many are chosen from each category. In some examples, it is ideal to display snippets of the EGM signal for all cardiac episodes resulting in treatment. However, in some instances this may be too many episodes, and it may be beneficial to select representatives of various subclassifications within the categories for display.

In some examples, VT/VF episodes may be prioritized by the number of shocks or ATPs needed to resolve the arrhythmia, with the first X number of episodes from a list ordered from most to least shocks selected. In some examples, the VT/VF category may be further divided by whether or not ATP was given. The episodes within each group may be ordered based on time of episode. The episodes selected may include at least one episode from each subgroup.

In some examples, processor 106, based on summary rules 96, may create subgroups based on the ratio of the atrial sensed event rate (A rate) to the ventricular sensed event rate (V rate). In some examples, the episodes may be further grouped based on whether the A rate matches the V rate, the A rate is less than the V rate, or the A rate is greater than the V rate. Processor 106 may prioritize the cardiac episodes within each sub group based how recently the cardiac episode occurred. In some examples, at least one cardiac episode is selected from each subgroup.

In some examples, the VT/VF episodes may be prioritized based on duration of the episode. The first predetermined number of cardiac episodes from a list ordered from longest to shortest duration may be selected. In some examples, the VT/VF episodes may be prioritized based on treatment severity or episode severity. Treatment severity may include a degree of morbidity, e.g., pain, given to the patient. In some examples, this may include the number of shocks within a specified period of time, energy output, or rate acceleration. In some examples, prioritization may be based on number of shocks, ATP, aborted shock, or number of shocks or ATPs. In some examples, episode severity may be based on the type of episode detected based on rate, e.g., a VF episode may be classified as more severe than a monomorphic VT episode. Episode severity may also be based on the type of episode detected based on morphology, i.e., a polymorphic rhythm may need to be treated with a shock versus a monomorphic rhythm that may be pace-terminated. In some examples treatment. A predetermined number of the cardiac episodes with the most severe treatment may be selected. In some examples, the VT/VF episodes may be prioritized based on time the cardiac episode occurred, with a predetermined number of the most recent cardiac episodes selected. In some examples, a predetermined number of episodes may be selected in a manner to be evenly spread over the time period the cardiac episodes cover. In some examples, certain types of episodes may be prioritized over other types of episodes within a fixed number of total episodes included in an EGM summary. For examples, more low priority episodes may be presented when less high priority episodes are available.

In some examples, a portion of the fixed number of VT/VF episodes selected may be chosen based on morphology of the beats, e.g., of the R-waves. For example, unique morphologies may be selected, or ones where the A sensed events to V sensed events have a 1 to 1 ratio with the A leading the beat, or with V leading the beat. In some examples, VT/VF episodes may be selected based on a classification confidence associated with the classification of the episode by processor 102 of external device 100 applying a retrospective analysis algorithm to the EGM data for the episode. For example, representative episodes may be selected from those episodes with a low algorithm classification confidence as well as those from those episodes having a high classification confidence. In some examples, representative episodes may be selected from groups of VT/VF having the same classification rationale or from those determined to be "inappropriate detections" or those which are unknown based on retrospective analysis. In some examples, episodes may be selected based on a combination of the factors presented above.

A 1-to-1 ratio of atrial sensed events to ventricular sensed events may be characterized by a period of time with the same number of atrial sensed events and ventricular sensed events, with the atrial and ventricular sensed events alternating. In order to determine which chamber is leading, a processor 106 may determine A-A interval lengths and V-V interval lengths. In the event that changes in interval length are consistently led by the atrium, the atrial is considered to lead the beat. In the event that changes in interval length are consistently led by ventricle, the ventricles are considered to be leading the beat.

The VT/VF episodes selected may be displayed along with the reason for the selection. For example, where various representative VT/VF episodes are selected, each cardiac episode may be displayed along with an indication of the class or group that the episode represents, such as which classification rationale it represents.

Processor 106 may select up to a fixed number of SVT episodes. SVT episodes may be prioritized based on time of the cardiac episodes within the category. In some examples, the most recent SVT episodes may be considered the given highest priority, with a predetermined number of the most recent SVT episodes selected. In some examples, any SVT episodes with unique reasons for withholding treatment may be selected, up to a predetermined number of SVT episodes. In some examples, the SVT episodes may be further grouped based on A rate versus V rate. In some examples, SVT episodes with the fastest V rate are prioritized.

Processor 106 may selected at least one episode from more than one group. In some examples, the groups may be based on morphology or retrospective analysis classification. In some examples, SVT episodes may be prioritized based on duration with a predetermined number of the most recent episodes selected some examples, a predetermined number of episodes may be selected in a manner to be evenly spread over the time period the cardiac episodes cover.

Processor 106 may select up to a fixed number of monitored VT episodes. The monitored VT episodes may be prioritized based on time the cardiac episode occurred, with a predetermined number of the most recent cardiac episodes in this category selected. In some examples, a cardiac episode with a significantly different V rate or a significantly different A rate then the rest of the cardiac episodes in the category may be selected. In some examples, the monitored VT episodes with the fastest V rate may be selected. In some examples, the monitored VT episodes with the longest duration may be selected. In some examples, representative monitored VT episodes may be selected based on retrospective analysis classification, if available. A combination of selection criteria may be used to select the monitored VT episodes to display. For example, the monitored VT episode with the fastest V rate, the episode with the longest duration and one or more episodes with significantly different V rates or A rates may be selected to reach a fixed number of monitored VT episodes for display.

Processor 106 may select up to a fixed number of VTNS episodes. The VTNS episodes may be prioritized based on time the cardiac episode occurred, with a predetermined number of the most recent cardiac episodes selected. In some examples, VTNS episodes may be prioritized based on the number of beats within the cardiac episode, with a predetermined number of the episodes with the largest number of beats selected. In some examples, VTNS episodes may be prioritized based the rate of beats, with a predetermined number of the episodes with the fastest beats, e.g., fastest beat, or fastest mean or median rate, being selected. In some examples, representative cardiac episodes may be selected from groups of VTNS episodes having similar retrospective analysis classifications. In some examples, the fixed number of VTNS episodes may be selected based on a combination of different priority schemes.

Processor 106 may select up to a fixed number of AT/AF episodes. The AT/AF episodes may be prioritized based on time the cardiac episode occurred, with a predetermined number of the most recent cardiac episodes selected. In some examples, the AT/AF episodes may be prioritized based on the length of the episodes, with a predetermined number of the longest duration cardiac episodes selected. In some examples, the AT/AF episodes may be prioritized based on V rate, with a predetermined number of cardiac episodes with the fastest V rate selected.

In some examples, the AT/AF episodes may be prioritized by degree of A-A interval regularity. In some examples, the cardiac episodes with the least degree of A-A interval regularity are prioritized. In some examples, the cardiac episodes with the highest degree of A-A interval regularity are prioritized. In some examples, processor 106 may select representative episodes from those AT/AF episodes with or without far-field R-waves. Processor 106 may also select representative AT/AF episodes based on retrospective analysis classification, if available. In some examples, the fixed number of AT/AF episodes may be selected using a combination of priority criteria.

In some examples, processor 106 may select up to a fixed number of VOS episodes. The VOS episodes may be prioritized based on the time the cardiac episode occurred, with a predetermined number of the most recent cardiac episodes selected. In some examples, processor 106 may also select VOS episodes on retrospective analysis classification.

After processor 106 selects a subset of episodes from each category of cardiac episodes (114), processor 106 prioritizes the cardiac episode categories for display (116). Summary rules 96 may store rules for prioritizing cardiac episode categories. The rules may be pre-programmed and may be customizable based on preferences of the physician. In some examples, treated VT/VF episodes may be displayed first, followed by monitored VT episodes, VTNS episodes, SVT episodes and AT/AF episodes. Further, within summary rules 96, rules for the order of episodes within each category may be included. The episodes may be displayed within each category based on the same prioritization rules used in selecting the episodes to display. For example, within each category grouping episodes may be displayed based on whether the retrospective analysis classification matches the classification made by IMD 16. Episodes may also be further prioritized based on classification confidence.

Processor 106 may also select a portion, referred to herein as a "snippet," of each selected cardiac episode for display (118). Summary rules 96 may store a default rule where a static section of the EGM signal is always shown. In some examples, the portion displayed may be customizable based on the preferences of a particular physician. The section of the EGM signal displayed may be the portion just before detection. That is an EGM snippet may be right aligned with the final beat leading to detection at the end. In some examples, the summary rules 96 may result in always showing the beginning of EGM storage for the particular episode, with the EGM snippet window left-aligned with the first EGM beat. An EGM snippet window may also be aligned with onset of the arrhythmia. This may be determined, for examples, based on a simple cycle length change in the pre-detection period. In some examples, summary rules 96 may include additional rules to determine when a portion other than the default portion should be displayed. For example, if an episode has a 1:1 A to V ratio for at least a portion of the episode, the onset of the 1:1 ratio may be the starting point of the EGM snippet window.

The size of the portion of the cardiac episode displayed may change depending on a variety of factors including, for example, the number of EGM signals to be displayed and the method used to select the EGM snippet window. For example, an EGM snippet window may show a portion of the EGM used by IMD 16 to make its final classification decision. In some examples the EGM snippet may include both the EGM before and after anti-tachycardia pacing, both the EGM before and after shock or episode termination, or enough of the EGM snipped to show a change in ventricular morphology. The portion of the snippet shown may also be based on information from the retrospective analysis performed by computing device 104. For example, a portion of the EGM signal where processor 106 has determined there is a likelihood of oversensing may be displayed. The portion of the EGM signal may also be different depending on whether IMD 16 had pre-storage on or off.

The portion of the EGM signal chosen for display may be labeled with the rational used for the selection of the location of the EGM snippet window. For example, an image of the EGM snippet may also include a label stating that the window is "showing EGM at ATP termination," "showing detection," or "showing onset," for example.

User interface 88 displays the subset of cardiac episodes (122) for viewing by a physician or other clinician. The display may include a thumbnail of the EGM snippet along with at least some additional information. The identifying information may include one or more of episode classification by IMD 16, a retrospective analysis classification by processor 106, rationale for retrospective analysis classification, reasoning for selection of the particular episode for display, response by IMD 16, time of episode, length of episode, or an episode number. In some examples, the initial EGM summary report may not include a thumbnail of the EGM snippet. Instead, a list of episodes, along with one or more pieces of additional information may be displayed. A user may select one or more of the cardiac episodes, for further analysis. If a cardiac episode is chosen, an image of the EGM snippet may be displayed. In some examples, the image is an enlarged image of the thumbnail. In some examples, the image may include more of the EGM signal than displayed in the thumbnail. In some examples, such as when there is no thumbnail of the EGM signal, the display resulting from selection of a cardiac episode may be the first opportunity for the user to view the selected EGM snippet.

Figure 7:
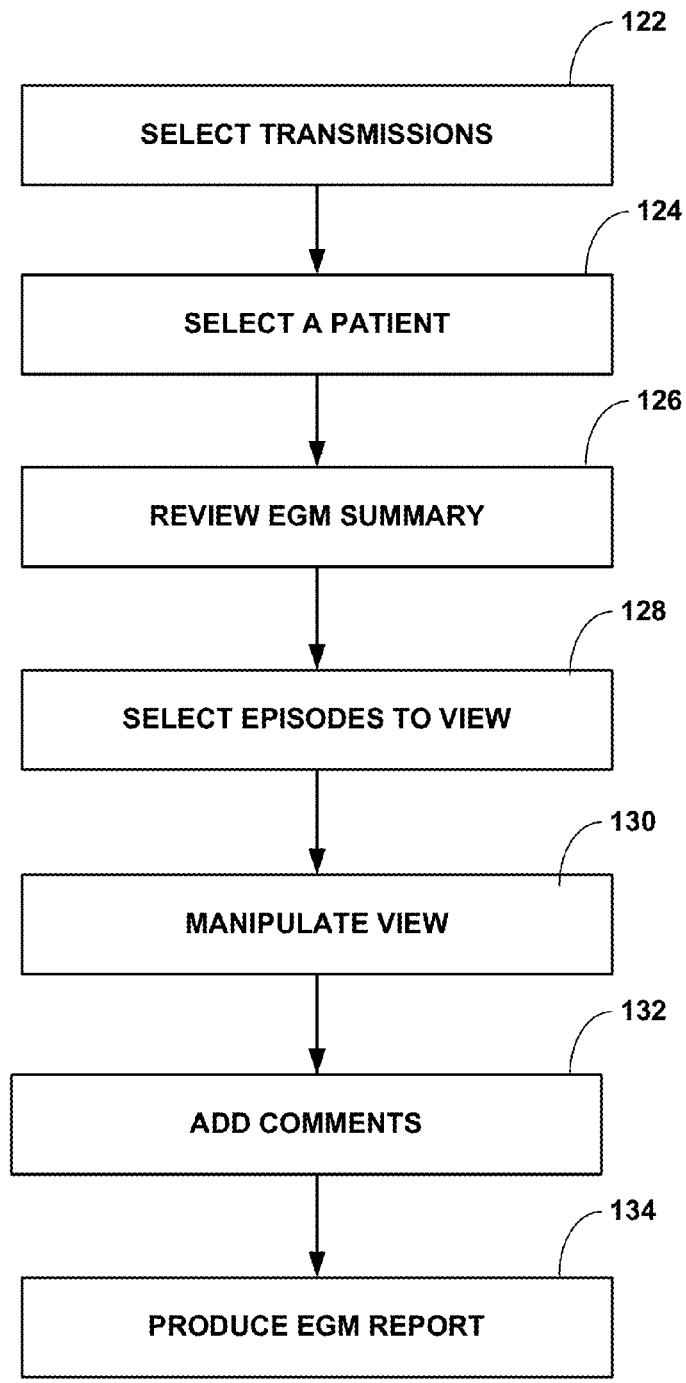
FIG. 7 is a flow diagram illustrating an example method of production an EGM report consistent with the present disclosure.

FIG. 7 is a flow diagram illustrating an example method for a user to produce an EGM report consistent with the present disclosure. A user may log on to a computing device 104 having a user interface 88. The computing device 104 may display a home screen that includes a number of options for physician or other clinician, including the ability to review transmissions transmitted from individual patients over network 98. In response to a user selection of transmission (122) user interface 88 may display a list of the physician's patients who have recently transmitted EGM signal information. The user may select a patient (124) for review of the transmitted EGM signal data. The selection may be made on information present along with the patient name including, for example, time of transmission, next appointment, or number of episodes transmitted.

In response to a patient selection, processor 106 may generate an EGM summary report according to the method of FIG. 6. The physician or other clinician may review the EGM summary (126) displayed via user interface 88. The EGM summary may include thumbnails of the episodes or other information useful for the physician in determining which episodes to select for more in depth review. Based on the review of the summary the physician may select episodes to view (128).

Figure 10:
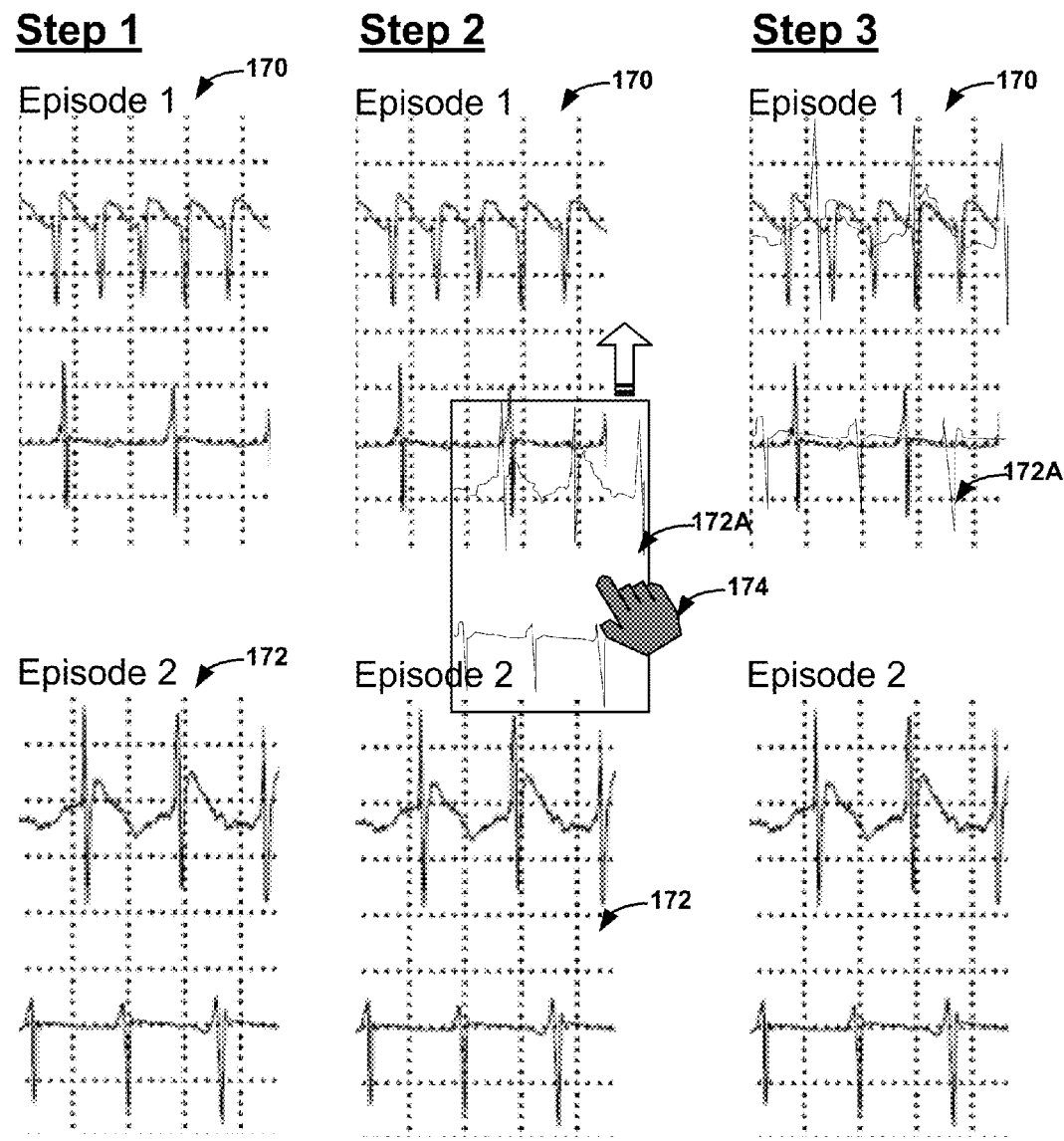
FIG. 10 illustrates an example method of comparing two EGM snippets.

In response to the selection of one or more cardiac episodes, an EGM snippet may be presented via user interface 88 as shown in FIG. 10, discussed in more detail below. The image may include both a portion of a marker channel, a portion of an EGM signal, and an interval plot thumbnail. In some examples, the view also includes information regarding detection and classification of the episode by IMD 16 and the classification of the episode using retrospective analysis by computing device 104.

Figure 9A:
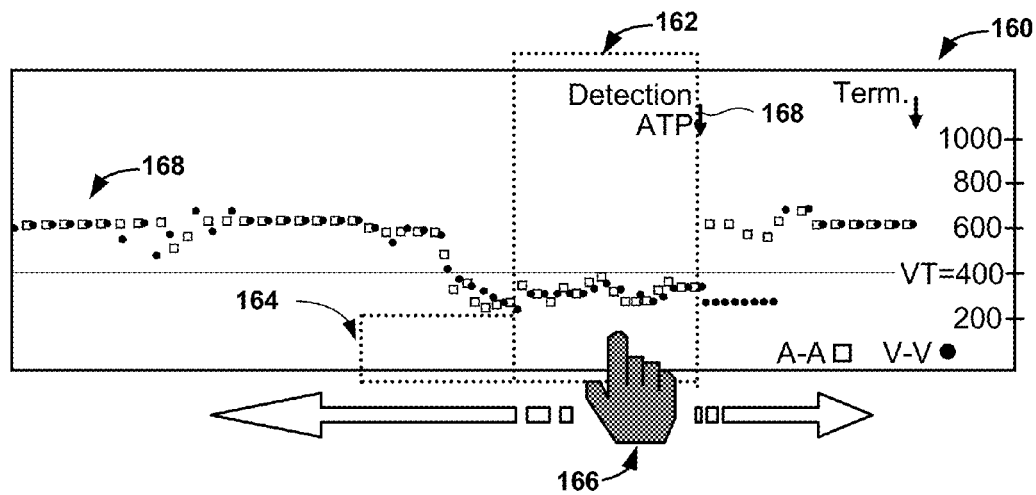
FIG. 9A illustrates an example interval plot for a cardiac episode detected by an IMD.
Figure 9B:
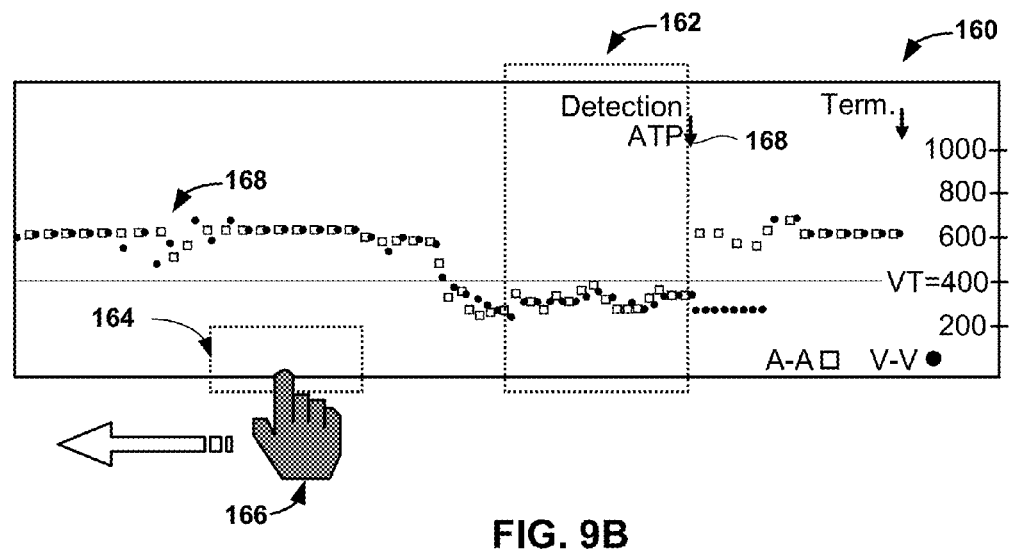
FIG. 9B illustrates another example interval plot for a cardiac episode detected by an IMD.

User interface 88 may allow the user to manipulate the view presented (130). For example, as shown in FIGS. 9A and 9B, the portion of the EGM signal displayed may be changed in response to user input. In some examples, the interval plot includes indications of which portion of the EGM signal and the marker channel are currently being displayed. As a default, a static section of the EGM is initially displayed. The user may interact with user interface 88 to change the view of the EGM snippet or the marker channel by manipulating the position of windows in the interval plot thumbnail. As the user moves the position of the window in the interval plot thumbnail, the content of the EGM snippet changes. The user may move the EGM window and the marker channel window together or separately.

In some examples, more than one cardiac episode may be displayed in greater detail. For example, a first cardiac episode and a second cardiac episode may be displayed on the user interface 88 at the same time. The user may compare the two episodes as described in greater detail below with respect to FIG. 10.

Based on the viewing and manipulation of a particular EGM snippet, a user may add comments (132) using user interface 88. The information inputted by the user may be displayed along with other information for a selected cardiac episode. In some examples, comments may have been added by processor 106. The user may also modify any comments presented by with the EGM snippet. The comments may include thoughts about what is displayed. For example, the user may add a comment with a classification based on the user's viewing of the EGM signal information. These comments may be stored in a database for future retrieval. In some examples, the comments may be included in the patient's EMR.

Processor 106 may produce an EGM report (134). The EGM report may be generated based on user input. For example, the EGM report may include cardiac episode selected by the user. The EGM report may also include any notes added by the user during review of the EGM summary.

The EGM report may be in the form of an electronic file. In some examples, a paper copy of the EGM report may be generated for placement within a patient's paper file.

Figure 8:
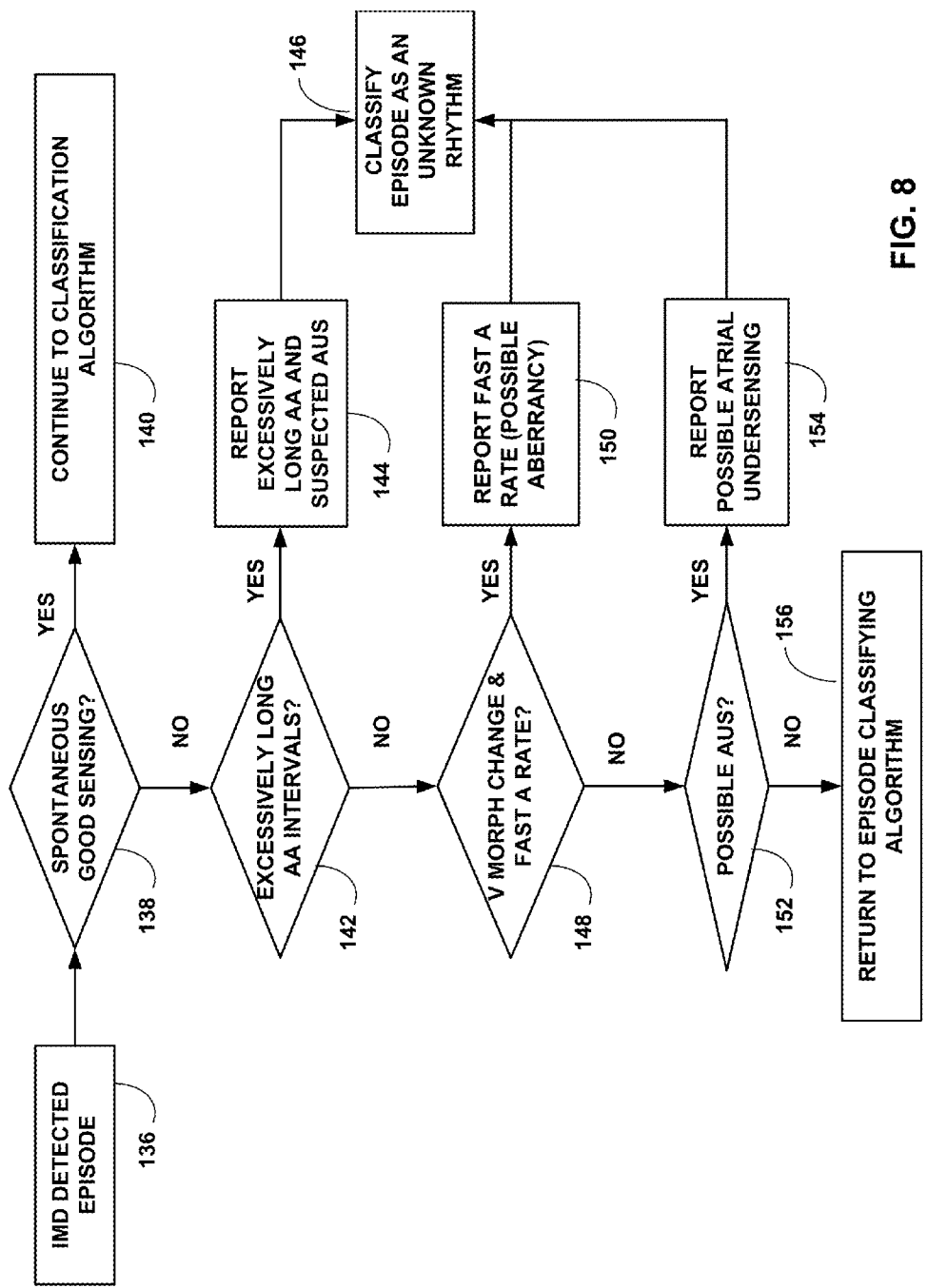
FIG. 8 is a flow diagram illustrating an example retrospective analysis algorithm consistent with examples in the present disclosure.

FIG. 8 is a flow chart of an example retrospective analysis algorithm consistent with examples in the present disclosure. Computing device 104 receives data transmitted from IMD 16 that includes one or more cardiac episodes. The episodes may be stored in memory 92. Processor 106 may retrieve an IMD 16 detected episode (136) from memory 92 for processing. Processor 106 determines whether the EGM signal for the detected episode indicates spontaneous good sensing (138). Spontaneous sensing occurs when a rhythm is not induced. Good sensing is sensing that does not include oversensing or undersensing of the EGM signal.

A determination of under-sensing may be based on a determination of whether one of a predetermined number of under-sensing criteria has been met. An example of an under-sensing criterion includes determining whether at least one sensed AA interval associated with predetermined beats, such as the NID ventricular beats prior to detection of the arrhythmia and the atrial interval immediately subsequent to the detection of the arrhythmia is greater than a predetermined interval, such as 2500 ms, for example. Another example of under-sensing criteria includes determining whether the atrial channel includes less than a predetermined number of events prior to detection. Other examples of under-sensing criteria are taught in U.S. Pat. No. 7,894,883 to Gunderson et al., incorporated herein by reference in its entirety. A determination of over-sensing may be based on a determination of ventricular oversensing (R-wave oversensing) or T-wave oversensing, for example.

If processor 106 determines the EGM signal indicates spontaneous good sensing, processor 106 continues to an episode classification algorithm (140) that may be stored in memory 92. The classification algorithm may determine whether the cardiac episodes should have been classified as VT/VF, SVT, or unknown, for example. In some examples, the classification algorithm may also determine if detection and classification by IMD 16 was inappropriate. If there is not spontaneous good sensing (138) then processor 106 examines the EGM signal data to determine a possible reason behind the lack of good sensing. Processor 106 may determine whether the EGM signal include excessively long A-A intervals (142). In some examples processor 106 may examine the marker channel to determine if excessively long A-A intervals are present. The A-A intervals may be compared to a predetermined threshold. In the event that processor 106 determines that the A-A interval is excessively long, the processor may report excessively long A-A intervals and suspected atrial under-sensing (AUS) (144). The processor then classifies the episodes as an unknown rhythm (146).

In some examples, the reporting of the excessively long A-A interval and suspected AUS (144) may include storing in memory 92 an indication of the long A-A interval along with the cardiac episode being analyzed. This may allow for a comment containing an indication of the suspected AUS to be presented along with an EGM snippet of the cardiac episode and the classification of unknown rhythm. In some examples, the indication may be including in the EGM summary report. The indication may also be presented when a user selects a particular cardiac episode to examine in greater detail, for example.

If processor 106 determines that the cardiac episode does not include excessively long A-A intervals (142), then the processor 106 may determine whether the cardiac episode includes a ventricular morphology change and a fast atrial rate (148). In some examples, the ventricular morphology occurs at approximately the same time as the fast atrial rate. If the ventricular morphology has change and a fast atrial rate is present, then processor 106 reports the fast atrial rate and the possibility that the episode is an aberrancy (150). Process 106 then classifies the cardiac episode as an unknown rhythm (146).

In some examples, the reporting of the fast A rate and possible aberrancy (150) may include storing in memory 92 an indication of the fast A rate and possible aberrancy along with the cardiac episode being analyzed. This may allow for a comment containing an indication of the possible aberrancy to be presented along with an EGM snippet of the cardiac episode and the classification of unknown rhythm. In some examples, the indication may be including in the EGM summary report. The indication may also be presented when a user selects a particular cardiac episode to examine in greater detail, for example.

If processor 106 determines that the cardiac episode does not include a combination of ventricular morphology change and a fast atrial rate, processor 106 continues to analyze the cardiac episode for other signs of possible AUS (152). For example, signs of AUS may include low atrial amplitude or extremely long atrial intervals. In some examples, processor 106 may look for consistent PR intervals when atrial sensed events are present and no atrial events associated with the other R-waves. If it is determined that the lack of spontaneous good sensing (138) may be a result of possible AUS (152), then processor 106 reports the possible AUS (154) and classifies the episode being analyzed as an unknown rhythm (146).

If the processor 106 does not detect possible AUS (152), then processor 106 may continue to an episode classification algorithm (140) stored in memory 92. The episode classification algorithm may be the same or different than the classification algorithm used in response to processor 106 determining spontaneous good sensing (138) is present. In some examples, the classification algorithm includes a determination of whether oversensing may have occurred. Example classification algorithms may be found in U.S. Pat. No. 7,894,883 to Gunderson et al., incorporated herein by reference in its entirety. In some examples, the classification algorithm may report the reason for the resulting classification of the cardiac episode. The reason for the classification may be stored along with the classification in memory 92. The reason may also be included in a summary of the cardiac episode presented to a user.

FIGS. 9A and 9B illustrate an example interval plot 160 for a cardiac episode detected by IMD 16 and transmitted to computing device 104. In FIG. 9A, interval plot 160 includes an EGM signal window 162 and a marker channel window 164. In FIG. 9A cursor 166 may be used to move EGM signal window 162 and marker channel window 164 together. In the example of FIG. 9A, EGM signal window 162 is positioned with the right side of the window aligned with the detection of tachycardia and the beginning of anti-tachycardia pacing (ATP) 168. In some examples, the depicted window locations may be a default position from which a user may move the EGM signal window 162 and marker channel window 164 to the left or right.

EGM signal channel window 162 indicates which portion of the EGM signal is presented to the user on user interface 88. The marker channel window 164 indicates a portion of the marker channel, in addition to the portion of the marker channel within the EGM signal channel, is presented to the user on user interface 88. As the windows move on the interval plot 160, the content of an EGM snippet presented to the user changes.

As shown in FIG. 9B, it may be possible to move the marker channel window 164 independently from the EGM signal channel window 162. In some examples, the marker channel window 164 and EGM signal channel window 162 shown in FIG. 9B are the same windows as marker channel window 164 and EGM signal channel 162 of FIG. 9A. The movement of either the marker channel window 164 or the EGM signal channel window 162 may allow for a user to examine a larger amount of the EGM signal data for a given cardiac episode. Moving the marker channel window 164 independently from the EGM signal channel window 162 may allow a user to examine the onset of a cardiac episode while also viewing the point of detection in the EGM snippet.

In some examples, processor 106 may determine where EGM signal window 162 and marker channel 164 are most likely to present a meaningful portion of the EGM signal. Processor 106 may select a portion by working backwards from detection to find the first of several slow intervals. In some examples, the processor may count back a number of intervals form the detection. The number counted back may be the NID. The portion shown would be assumed to be onset of the arrhythmia. In some examples, the default setting may to have marker channel window 164 show from onset of the arrhythmia forward and the EGM snippet window show from detection back.

FIG. 10 illustrates an example method of comparing two EGM snippets from two episodes retrieved from an IMD. As shown in FIG. 10, a user may select a first EGM snippet from a first episode (170) and a second EGM snippet from a second episode (172) for comparison. The two episodes may be displayed proximate to each other in step 1. Any intervening episodes may be hidden so the two episodes are directly adjacent one another. In other examples, the selected episodes may be displayed on a new view including only the episodes selected. Although FIG. 10 illustrates the comparison between two selected episodes, it may be possible for 3 or more episodes to be compared in a similar manner. In step 2, cursor 174 may be used to select second episode snippet 172 and start to drag a copy of the second episode snippet 172A towards first episode 170. In step 2, the second episode copy 172A overlaps with episode 170. This may allow a user to compare the morphology of two EGM snippets.

In some examples, a user may select two cardiac episodes having similar classifications. For example, two cardiac episodes that were detected and classified by IMD 16 as VT/VF may be compared. In some examples, the two cardiac episodes selected may have the same IMD 16 classification, but different classifications during retrospective analysis. In still other examples, an episode may be compared to a current EGM snippet. The current EGM snippet may be a portion of a patient 12's EGM signal collected at the time of transmission. The EGM signal for a selected EGM signal may be laid over the current EGM signal snippet in order to provide a visual comparison of the selected cardiac episode and the patient's EGM signal at time of transmission. In some examples, the two cardiac episodes selected may be from different transmissions from IMD 16. For example, the current EGM snippet from the most recent transmission may be compared to the EGM snippet from the time of transmission for a previous transmission from IMD 16.

Figure 11:
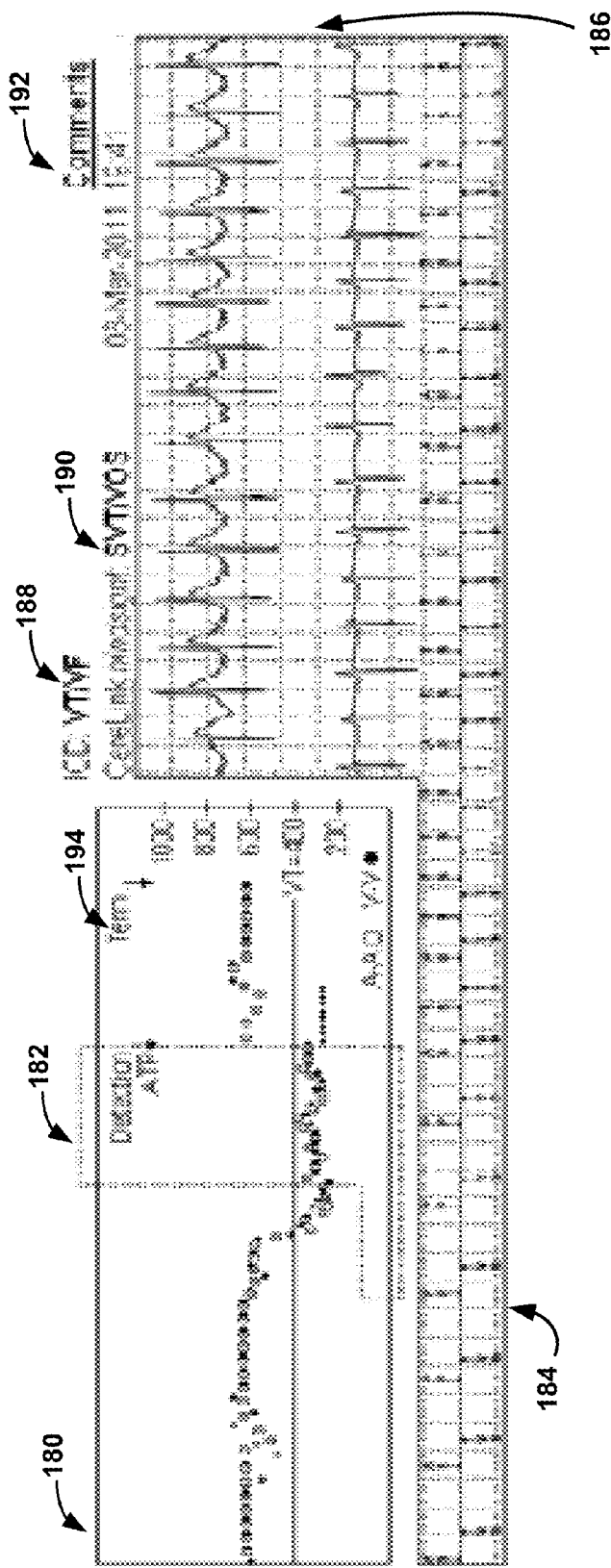
FIG. 11 illustrates an example display of a cardiac episode.

FIG. 11 illustrates an example display on user interface 88 for a single cardiac IMD detected episode. The display may include an interval plot 180 with a window 182 indicating which portion of the cardiac episode is currently displayed. The display may include a portion of the marker channel 184 and a portion of the EGM signal 186. The portions displayed may be selected as described above with respect to FIGS. 9A and 9B.

The display may also include a number of comments. For example, the display may include the detection classification 188 that was provided by IMD 16. In examples where retrospective analysis has been performed, the display may also include a retrospective classification 190. The display may also include a way to provide comments 192. In some examples, clicking on comments may open an additional window in which the user may add comments regarding the user's thoughts about what is presented. In some examples, annotations or comments may be made anywhere on the EGM signal or other portion of the display. For example, annotation 194 indicates the termination of the arrhythmia. In some examples, comments or annotations made on an EGM snippet may be included in the EGM summary report along with a thumbnail of the cardiac episode. The comments may also be a part of the final EGM report generated based on user selections. In some examples, the comments on the final EGM report may include a rationale for where the EGM snippet window is placed, such as "showing EGM at onset" or "showing EGM at ATP termination."

FIGS. 12A-12D illustrate various example timelines of cardiac episodes. In each timeline includes an indication of when cardiac episodes included in the transmission occurred. Each timeline may include cardiac episodes from a single transmission of from multiple transmissions from the same IMD.

Figure 12A:
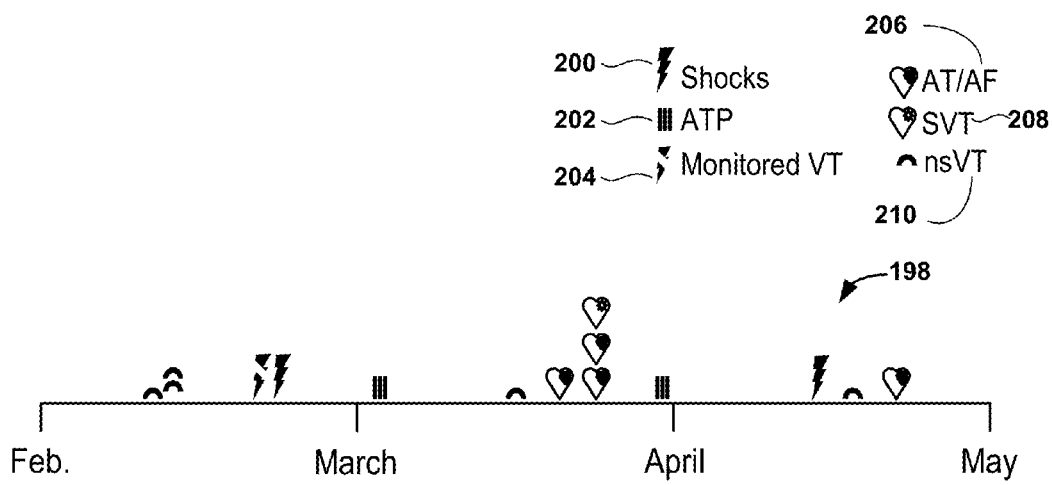
FIGS. 12A-12D illustrate example cardiac episodes timelines.

FIG. 12A illustrates a timeline 198 of cardiac episodes transmitted from IMD 16 to computing device 104. The timeline 198 may be included as a portion of an EGM summary report. The timeline 198 may include icons that indicate cardiac episode classifications that may be made by IMD 16 and, when placed on the timeline 198, indicate different times at which such classifications were made by the IMD. The icons may include shocks 200, ATP 202, monitored VT 204, AT/AF 206, SVT 208 and VTNS 210. In some examples, the icons may be EGM snippets. The timeline 198 may include icons for each cardiac episode included in the transmission. In some examples, a subset of cardiac episodes selected for inclusion in the EGM summary report may be represented on the timeline.

Figure 12B:
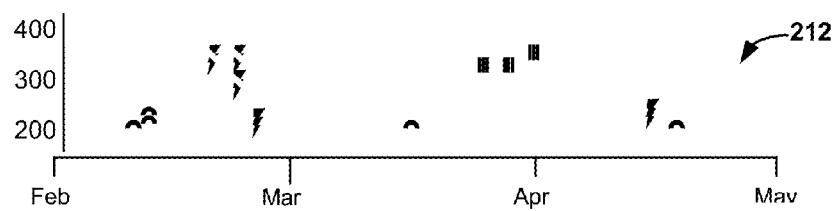

FIG. 12B illustrates a timeline 212 of cardiac episodes. The graphical timeline shows icons indicating what time the cardiac episode occurred based on classification by IMD 16. In addition, the graph indicates the cycle length for each of the cardiac episodes via the positioning of the icons on the vertical scale (Y-axis). The cycle length may be the mean or median cycle length for each interval within the cardiac episode, as an example.

Figure 12C:
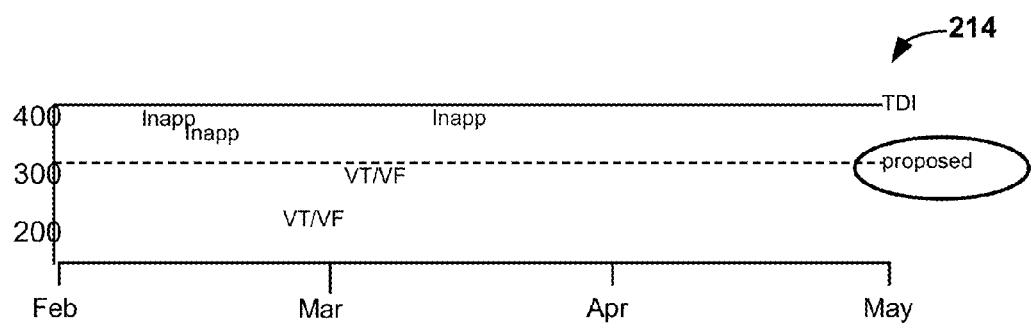

FIG. 12C illustrates a timeline 214 of cardiac episodes. The timeline graphically depicts episodes by classification based on retrospective analysis. In the example in FIG. 12C, whether the cardiac episode was inappropriately classified by IMD 16 or whether the episode was VT/VF. In addition, similar to FIG. 12B, the positioning of the icons on the vertical scale indicates the cycle length of the cardiac episode In some examples the graph may include an indication of TDI used by IMD 16 as well as a suggested TDI for future programming of IMD 16. For example, as shown in FIG. 12C, processor 106 may suggest a proposed TDI that excludes the cycle lengths that resulted in inappropriate classification by IMD 16. The proposed TDI may more accurately separate true VT/VF from inappropriate episodes.

Figure 12D:
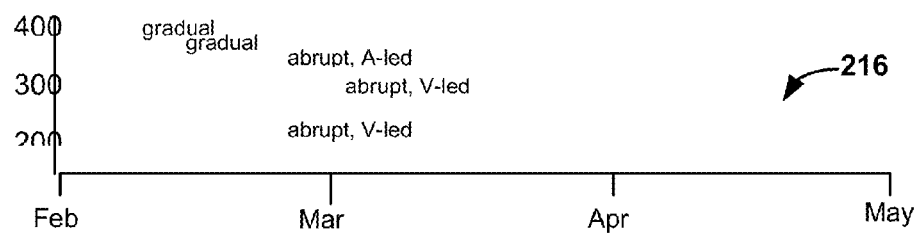

FIG. 12D illustrates a graphical timeline 216 that shows episode characteristics. The episode characteristics are located one the vertical axis with respect to average cycle length and on the horizontal axis with respect to the timing of the episode. In some examples, information from changes in cycle length, or leading chamber may be shown on the graph. Other information that may be included on the graph may be, for example, the reason for the classification as a particular cardiac episode. In the graph of FIG. 12D the characteristics are graphed against the cycle length and the date of the cardiac episode.

One or more graphical timelines not shown in FIGS. 12A-12D may be creating by graphing information from one or more of the graphs depicted. For example, a graphical timeline may include cycle length, classification by IMD 16, and classification by computing device 104.

The techniques described in this disclosure may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

What is claimed is:

1. A method comprising:

receiving cardiac electrogram (EGM) signal data from an implantable medical device (IMD), the EGM signal data including a plurality of detected cardiac episodes, each of the plurality of cardiac episodes classified by the IMD as at least one of a ventricular tachycardia/ventricular fibrillation (VT/VF) episode, a supraventricular tachycardia (SVT) episode, a ventricular tachycardia non-sustained (VTNS) episode, an atrial tachycardia/atrial fibrillation (AT/AF) episode, a monitored VT episode, or a ventricular oversensing (VOS) episode;

conducting a retrospective analysis of each of the plurality of cardiac episodes, the retrospective analysis providing a retrospective analysis classification;

using at least one processor, creating, for each cardiac episode category, a subset of the plurality of cardiac episodes, each subset including greater than or equal to one episode and less than or equal to a predetermined number of episodes; and selecting, using the at least one processor, a respective subset of the plurality of cardiac episodes for display based at least in part on at least one of the IMD classification and the retrospective analysis classification.

2. The method of claim 1, further comprising displaying a thumbnail of a portion of the EGM signal for each of the subset of the plurality of cardiac episodes.

3. The method of claim 2, further comprising selecting the portion of the EGM signal in the thumbnail based on a portion of the EGM signal used to make the retrospective analysis classification.

4. The method of claim 1, further comprising displaying information associated with the respective subset of the plurality of cardiac episodes selected for display.

5. The method of claim 4, wherein the information displayed for the respective subset of the plurality of cardiac episodes includes an indication of the IMD classification and an indication of the retrospective analysis classification.

6. The method of claim 4, wherein the information displayed for the respective subset of the plurality of cardiac episodes includes notes, generated by a processor, regarding a basis for the retrospective analysis classification.

7. The method of claim 1, further comprising prioritizing each type of IMD classification based on EGM summary rules, and displaying the selected cardiac episodes based at least in part on the prioritization.

8. The method of claim 7, further comprising prioritizing the selected cardiac episodes within each IMD classification type based on EGM summary rules.

9. The method of claim 1, wherein selection of the respective subset of cardiac episodes is based at least in part on both the IMD classification and the retrospective analysis classification.

10. The method of claim 1, further comprising selecting, from the plurality of cardiac episodes, one or more VT/VF episodes with a unique morphology.

11. The method of claim 1, wherein the respective subset of the plurality of cardiac episodes comprises each of the plurality of cardiac episodes with a conflicting IMD classification and retrospective analysis classification.

12. The method of claim 1, wherein the predetermined number of episodes varies among each cardiac episode category.

13. The method of claim 1, wherein the predetermined number of episodes is substantially a same among each cardiac episode category.

14. The method of claim 1, wherein the predetermined number of episodes for a respective subset of a respective cardiac episode category is less than a total number of episodes for the respective cardiac episode category.

15. The method of claim 1, wherein selecting, using the processor, the respective subset of the plurality of cardiac episodes for display based at least in part on at least one of the IMD classification and the retrospective analysis classification comprises automatically selecting, using the processor, the respective subset of the plurality of cardiac episodes for display based at least in part on at least one of the IMD classification and the retrospective analysis classification.

16. A system comprising:
a communication module configured to receive electrogram (EGM) signal data from an implantable medical device, the EGM signal data including a plurality of cardiac episodes, each of the plurality of each of the plurality of cardiac episodes classified by the implantable medical device as at least one of a ventricular tachycardia/ventricular fibrillation (VT/VF) episode, a supraventricular tachycardia (SVT) episode, a ventricular tachycardia no stimulation (VTNS) episode, an atrial tachycardia/atrial fibrillation (AT/AF) episode, a monitored VT episode, or a ventricular oversensing (VOS) episode;

a processor configured to:
conduct a retrospective analysis for each of the plurality of cardiac episodes, the retrospective analysis providing a retrospective analysis classification;
create, for each cardiac episode category, a subset of the plurality of cardiac episodes, each subset including greater than or equal to one episode and less than or equal to a predetermined number of episodes; and
select a respective subset of the plurality of cardiac episodes for display based at least in part on at least one of the implantable medical device classification and the retrospective analysis classification; and a graphical user interface configured to display a summary of the selected respective subset of the plurality of cardiac episodes.

17. The system of claim 16, wherein graphical user interface is further configured to display a thumbnail of a portion of the EGM signal for each of the subset of the plurality of cardiac episodes.

18. The system of claim 17, wherein the processor is further configured to select the portion of the EGM signal in the thumbnail based on a portion of the EGM signal used to make the retrospective analysis classification.

19. The system of claim 16, further comprising a graphical user interface configured to display information associated with each of the respective subset of the plurality of cardiac episodes selected for display.

20. The system of claim 19, wherein the information displayed for each of the respective subset of the plurality of cardiac episodes includes an indication of the IMD classification and an indication of the retrospective analysis classification.

21. The system of claim 19, wherein the information displayed for each of the respective subset of the plurality of cardiac episodes includes notes, generated by the processor, regarding a basis for the retrospective analysis classification.

22. The system of claim 16, wherein the processor is further configured to prioritize each type of IMD classification for display on the graphical user interface, and the graphical user interface is further configured to display the selected cardiac episodes based at least in part on the prioritization.

23. The system of claim 22, wherein the processor is further configured to prioritize each type of IMD classification based on EGM summary rules.

24. The system of claim 16, wherein the processor is further configured to select, from the plurality of cardiac episodes, one or more VT/VF episodes with a unique morphology.

25. The system of claim 16, wherein the processor is further configured to select as part of the subset each of the plurality of cardiac episodes with a conflicting IMD classification and retrospective analysis classification.

26. The system of claim 16, wherein the processor is further configured to select the respective subset of cardiac episodes is based at least in part on both the IMD classification and the retrospective analysis classification.

27. The system of claim 16, wherein the predetermined number of episodes varies among each cardiac episode category.

28. The system of claim 16, wherein the predetermined number of episodes is substantially a same among each cardiac episode category.

29. The system of claim 16, wherein the predetermined number of episodes for a respective subset of a respective cardiac episode category is less than a total number of episodes for the respective cardiac episode category.

30. The system of claim 16, wherein the processor is configured to automatically select the respective subset of the plurality of cardiac episodes for display based at least in part on at least one of the IMD classification and the retrospective analysis classification.

31. A computer-readable medium containing instructions, the instructions cause a programmable processor to:
receive cardiac electrogram (EGM) signal data from an implantable medical device (IMD), the EGM signal data including a plurality of detected cardiac episodes, each of the plurality of cardiac episodes classified by the IMD as at least one of a ventricular tachycardia/ventricular fibrillation (VT/VF) episode, a supraventricular tachycardia (SVT) episode, a ventricular tachycardia non-sustained (VTNS) episode, an atrial tachycardia/atrial fibrillation (AT/AF) episode, a monitored VT episode, or a ventricular oversensing (VOS) episode;
conduct a retrospective analysis of each of the plurality of cardiac episodes, the retrospective analysis providing a retrospective analysis classification;
create, for each cardiac episode category, a subset of the plurality of cardiac episodes, each subset including greater than or equal to one episode and less than or equal to a predetermined number of episodes; and
select a respective subset of the plurality of cardiac episodes for display based at least in part on at least one of the IMD classification and the retrospective analysis classification.

32. A system comprising
means for receiving cardiac electrogram (EGM) signal data from an implantable medical device (IMD), the EGM signal data including a plurality of detected cardiac episodes, each of the plurality of cardiac episodes classified by the IMD as at least one of a ventricular tachycardia/ventricular fibrillation (VT/VF) episode, a supraventricular tachycardia (SVT) episode, a ventricular tachycardia non-sustained (VTNS) episode, an atrial tachycardia/atrial fibrillation (AT/AF) episode, a monitored VT episode, or a ventricular oversensing (VOS) episode;
means for conducting a retrospective analysis of each of the plurality of cardiac episodes, the retrospective analysis providing a retrospective analysis classification;
means for creating, for each cardiac episode category, a subset of the plurality of cardiac episodes, each subset including greater than or equal to one episode and less than or equal to a predetermined number of episodes; and
means for selecting, using a processor, a subset of the plurality of cardiac episodes for display based at least in part on at least one of the IMD classification and the retrospective analysis classification.

* * * * *

UNITED STATES PATENT AND TRADEMARK OFFICE
CERTIFICATE OF CORRECTION

PATENT NO.         : 8,744,560 B2
APPLICATION NO.    : 13/250676
DATED              : June 3, 2014
INVENTOR(S)        : Bruce D. Gunderson et al.

It is certified that error appears in the above-identified patent and that said Letters Patent is hereby corrected as shown below:

Claims

Col. 30, line 27, claim 19 delete "for each of the respective subset" and insert in place thereof -- for the respective subset --;

Col. 30, line 30, claim 20 delete "for each of the respective subset" and insert in place thereof -- for the respective subset --;

Col. 30, line 35, claim 21 delete "for each of the respective subset" and insert in place thereof -- for the respective subset --;

Col. 32, line 1, claim 32 delete "A system comprising" and insert in place thereof -- A system comprising: --.

Signed and Sealed this
Twenty-ninth Day of March, 2016

Michelle K. Lee
*Director of the United States Patent and Trademark Office*